US011589780B2

(12) United States Patent
Kuo et al.

(10) Patent No.: US 11,589,780 B2
(45) Date of Patent: Feb. 28, 2023

(54) ORAL APPLIANCE FOR MEASURING HEAD MOTIONS BY ISOLATING SENSORS FROM JAW PERTURBANCE

(71) Applicant: The Board of Trustees of the Leland Stanford Junior University, Stanford, CA (US)

(72) Inventors: Calvin Kuo, Stanford, CA (US); Lyndia Chun Wu, Stanford, CA (US); Kaveh Laksari, Stanford, CA (US); David B. Camarillo, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 523 days.

(21) Appl. No.: 15/373,454

(22) Filed: Dec. 8, 2016

(65) Prior Publication Data

US 2017/0156635 A1 Jun. 8, 2017

Related U.S. Application Data

(60) Provisional application No. 62/264,721, filed on Dec. 8, 2015.

(51) Int. Cl.
*A61B 5/11* (2006.01)
*A61B 5/00* (2006.01)
*A61B 5/103* (2006.01)
*A63B 71/08* (2006.01)

(52) U.S. Cl.
CPC .............. *A61B 5/11* (2013.01); *A61B 5/1036* (2013.01); *A61B 5/1114* (2013.01); *A61B 5/682* (2013.01); *A61B 5/7221* (2013.01); *A61B 2503/10* (2013.01); *A61B 2562/0219* (2013.01); *A63B 71/085* (2013.01)

(58) Field of Classification Search
CPC ....... A61B 5/11; A61B 5/682; A61B 2503/10; A61B 2562/0219; A63B 71/085
See application file for complete search history.

(56) References Cited

U.S. PATENT DOCUMENTS

| | | | | |
|---|---|---|---|---|
| 4,765,324 A | * | 8/1988 | Lake, Jr. | A63B 71/085 128/861 |
| 5,190,051 A | * | 3/1993 | Wilson | A61F 5/566 600/590 |
| 6,089,864 A | * | 7/2000 | Buckner | A61F 5/56 433/6 |
| 6,491,037 B1 | * | 12/2002 | Mortenson | A61B 5/01 128/859 |
| 8,215,312 B2 | * | 7/2012 | Garabadian | A61F 5/566 128/848 |
| 8,459,267 B2 | * | 6/2013 | Zimmerman | A63B 71/085 128/861 |

(Continued)

OTHER PUBLICATIONS

Kuo, C. et al. (2016) "Effect of the mandible on mouthgard measurements of head kinematics," Journal of Biomechanics 49(9):1845-1853.

*Primary Examiner* — Sean P Dougherty
(74) *Attorney, Agent, or Firm* — Foley & Lardner LLP

(57) ABSTRACT

An oral appliance includes: 1) a body defining a channel to accommodate an upper dentition; and 2) a motion sensor. The body includes a front portion defining a recess, and the motion sensor is affixed to the front portion.

10 Claims, 25 Drawing Sheets

(56) References Cited

U.S. PATENT DOCUMENTS

| | | | | |
|---|---|---|---|---|
| D710,506 S | * | 8/2014 | Tolentino | D24/181 |
| D743,108 S | * | 11/2015 | Charlton | D29/108 |
| D752,295 S | * | 3/2016 | Lovat | D29/108 |
| D760,441 S | * | 6/2016 | Cody | D29/108 |
| 10,028,679 B2 | * | 7/2018 | Paris | A61B 5/682 |
| 2005/0067816 A1 | * | 3/2005 | Buckman | A61B 5/6804 |
| | | | | 280/730.1 |
| 2005/0284489 A1 | * | 12/2005 | Ambis | A63B 71/085 |
| | | | | 128/859 |
| 2007/0151568 A1 | * | 7/2007 | Maurello | A63B 71/085 |
| | | | | 128/859 |
| 2009/0220921 A1 | * | 9/2009 | Abolfathi | A61B 5/02438 |
| | | | | 433/229 |
| 2011/0290261 A1 | * | 12/2011 | Spainhower | A61C 7/08 |
| | | | | 128/859 |
| 2012/0090625 A1 | * | 4/2012 | Evans | A63B 71/085 |
| | | | | 128/861 |
| 2013/0211270 A1 | * | 8/2013 | St. Laurent | A61B 5/4875 |
| | | | | 600/508 |
| 2013/0253286 A1 | * | 9/2013 | Fridman | A61B 5/682 |
| | | | | 600/301 |
| 2014/0187875 A1 | * | 7/2014 | Paris | A61B 5/682 |
| | | | | 600/301 |
| 2014/0188010 A1 | * | 7/2014 | Paris | A61B 5/1126 |
| | | | | 600/595 |
| 2014/0257051 A1 | | 9/2014 | Cam et al. | |
| 2014/0312834 A1 | | 10/2014 | Tanabe et al. | |
| 2015/0119759 A1 | * | 4/2015 | Gonzales | A63B 71/085 |
| | | | | 600/595 |
| 2016/0158628 A1 | * | 6/2016 | Layzell | A63B 71/08 |
| | | | | 128/862 |
| 2016/0262694 A1 | * | 9/2016 | Calcano | G01L 5/0052 |

\* cited by examiner

ORAL APPLIANCE FOR MEASURING HEAD MOTIONS BY ISOLATING SENSORS FROM JAW PERTURBANCE

CROSS-REFERENCE TO RELATED APPLICATION

This application claims the benefit of U.S. Provisional Application No. 62/264,721, filed Dec. 8, 2015, the content of which is incorporated herein by reference in its entirety.

STATEMENT REGARDING FEDERALLY SPONSORED RESEARCH OR DEVELOPMENT

This invention was made with Government support under contract EB017611 awarded by the National Institutes of Health. The Government has certain rights in the invention.

BACKGROUND

Concussion and other brain injuries resulting from severe head impacts are a leading cause of death or disability among children and young adults. Sub-concussive head impacts were originally thought to be relatively harmless due to the lack of immediate neurological symptoms; however, a growing body of evidence shows that the cumulative effects of multiple sub-concussive and concussive head impacts can accelerate the onset of Alzheimer's, Parkinson's and other neurodegenerative diseases.

There are many unanswered questions behind the neuroscience of concussion and these questions will remain so without a validated measurement technique. Efforts to model brain biomechanics have been made. However, questions remain about what force levels could lead to a concussive event or whether this threshold changes with age, gender, or type of activity. One promising hypothesis in the field is that white matter injury explains the typical transient symptoms of concussion that last for a few weeks. The hypothesis is that rotation of the head is transmitted into elongation of axons, which varies by the direction in which the head is rotated. As axons are rapidly elongated, microtubules slide past one another by stretching the tau protein that connects filaments. Excessive elongation causes rupture of the tau protein connections, cargo trafficking deficiency, and rupture of the plasma membrane. The massive ion flux caused by this disruption leads to a neurochemical and metabolic cascade, which explains both the increased vulnerability after concussion as well as the two-week time course of recovery stress. This hypothesis is based primarily on in vitro and animal experiments, with a small amount of human data from clinically diagnosed concussions that were reconstructed in the laboratory and simulated in finite element models.

Further, important questions in the field relate to neurodegeneration that may appear later in life due to repetitive concussive or sub-concussive blows. For example, it would be beneficial to know how many sub-concussive or concussive blows significantly increase the risk of Alzheimer's, chronic traumatic encephalopathy, or other neurodegenerative diseases.

Additionally, although it has been documented that vulnerability to concussion increases during the recovery after an initial injury, it is unclear if the force level to cause concussion is actually reduced if a patient is less able to avoid dangerous situations, or simply if the likelihood to report symptoms of concussion is increased.

Thus, there is a need to identify the underlying biomechanical and neurobiological mechanism of head impacts to properly treat, diagnose, and prevent short-term brain injury and long-term neurodegeneration. To understand the underlying biomechanical and neurobiological mechanism of head impacts, a relationship between head impact acceleration and neurological deficits should first be characterized.

To measure head impact acceleration, studies have relied on data from sensors that are constrained in their ability to fully characterize head motions, or on reconstructions of concussive football impacts using non-biofidelic dummy tests. The reliance on imperfect data has led to conflicting conclusions on the mechanism of injury and unreliable brain injury metrics.

Once the biomechanical and neurobiological mechanism of head impacts is understood, preventive measures may be evaluated. Once a relationship between head impact acceleration and neurological deficits is determined, detection of injury may be improved. Real-time measurements of head impacts on the field would provide an ability to quantify the severity of head impacts and count the occurrence of various types of head impacts. Quantifying the severity of head impacts is useful for real-time diagnosis of concussions, which is important because an initial concussion can increase the vulnerability to a second concussion. Counting the occurrence of head impacts is important because repetitive concussive and sub-concussive head impacts can accelerate the onset of long-term neurodegeneration. The current protocol for monitoring brain health involves on field observations and neuropsychological sideline tests to quantify head impact severity and diagnose concussions, and video analysis to count the occurrence of head impacts. Unfortunately, these techniques are subjective, costly, and cannot be implemented in real-time.

It is against this background that a need arose to develop the embodiments described in this disclosure.

SUMMARY

One aspect of this disclosure relates to an oral appliance. In some embodiments, the oral appliance includes: 1) a body defining a channel to accommodate an upper dentition; and 2) a motion sensor. The body includes a front portion defining a recess, and the motion sensor is affixed to the front portion.

In some embodiments, the front portion is formed to accommodate an incisor area of the upper dentition.

In some embodiments, the body further includes a pair of rear portions connected through the front portion, and the front portion defines the recess between the rear portions.

In some embodiments, the rear portions include respective standoff regions.

In some embodiments, the motion sensor includes at least one of an accelerometer or a gyroscope.

In some embodiments, the motion sensor has a data sampling rate of about 1 kHz or greater.

In some embodiments, the channel and the recess have opposite orientations or face opposite directions. For example, the channel can be formed on an upper side or surface of the body, while the recess can be formed on an opposite, lower side or surface of the body.

Another aspect of this disclosure relates to an oral appliance. In some embodiments, the oral appliance includes: 1) a body defining a channel to accommodate an upper dentition; and 2) a motion sensor affixed to the body. The body includes a standoff region sized to extend into a bite plane.

In some embodiments, the body includes a front portion and a pair of rear portions connected through the front portion, and the rear portions include respective standoff regions.

In some embodiments, the motion sensor is affixed to the front portion.

In some embodiments, the front portion defines a recess between the standoff regions.

In some embodiments, the motion sensor includes at least one of an accelerometer or a gyroscope.

Another aspect of this disclosure relates to an oral appliance. In some embodiments, the oral appliance includes: 1) a body defining a channel to accommodate an upper dentition; 2) a retainer connected to the body and sized to accommodate an upper palate; and 3) a motion sensor affixed to the retainer.

In some embodiments, the oral appliance further includes struts connecting the retainer to the body.

In some embodiments, the motion sensor includes at least one of an accelerometer or a gyroscope.

In some embodiments, the motion sensor has a data sampling rate of 1 kHz or greater.

Another aspect of this disclosure relates to an oral appliance. In some embodiments, the oral appliance is an instrumented mouthguard including: 1) a body formed to fit an upper dentition; and 2) at least one sensor positioned adjacent to the dentition and configured to sense motion of an area of the dentition. The mouthguard is configured to isolate sensed motion of the area of the dentition from perturbance of a lower jaw.

In some embodiments, the mouthguard further includes a bite force sensor or a jaw perturbance sensor, and the sensed motion is isolated from the perturbance of the lower jaw by adjusting the sensed motion according to measurements from the jaw perturbance sensor.

A further aspect of this disclosure relates to an oral appliance. In some embodiments, the oral appliance is an instrumented mouthguard including: 1) a body; and 2) at least one motion sensor positioned on an upper dentition or upper palate. The mouthguard is configured to isolate a skull motion from a mouthguard motion.

Other aspects and embodiments of this disclosure are also contemplated. The foregoing summary and the following detailed description are not meant to restrict this disclosure to any particular embodiment but are merely meant to describe some embodiments of this disclosure.

BRIEF DESCRIPTION OF THE DRAWINGS

For a better understanding of the nature and objects of some embodiments of this disclosure, reference should be made to the following detailed description taken in conjunction with the accompanying drawings.

DESCRIPTION

Embodiments of this disclosure are directed to a wearable oral appliance for measuring head motions. In some embodiments, the oral appliance is implemented as an instrumented mouthguard for measuring head impact data, and the mouthguard exhibits high acceleration and velocity measurement accuracy, improved data sampling rate, and high impact detection accuracy. In some embodiments, the oral appliance provides improved measurement accuracy by isolating sensors from jaw or mandible perturbance. The mouthguard of some embodiments of this disclosure provides for collecting of reliable data, which can be used to find relationships between head impact motion and acute or chronic neurological deficit.

By way of comparison, helmet-mounted sensors can suffer from an indirect coupling to the skull, which can cause significant error in head impact acceleration measurements, and helmet-mounted sensors are inapplicable in many sports played without helmets. Similarly, skin-mounted sensors can suffer from high error in impact acceleration measurements. Further, various other sensors have insufficient data sampling rates and are constrained in measuring fast motions commonly seen in head impacts. The inability to accurately measure head impact motions and sufficiently sample fast motions can skew results that rely on such comparative sensor measurements.

Figure 1A:
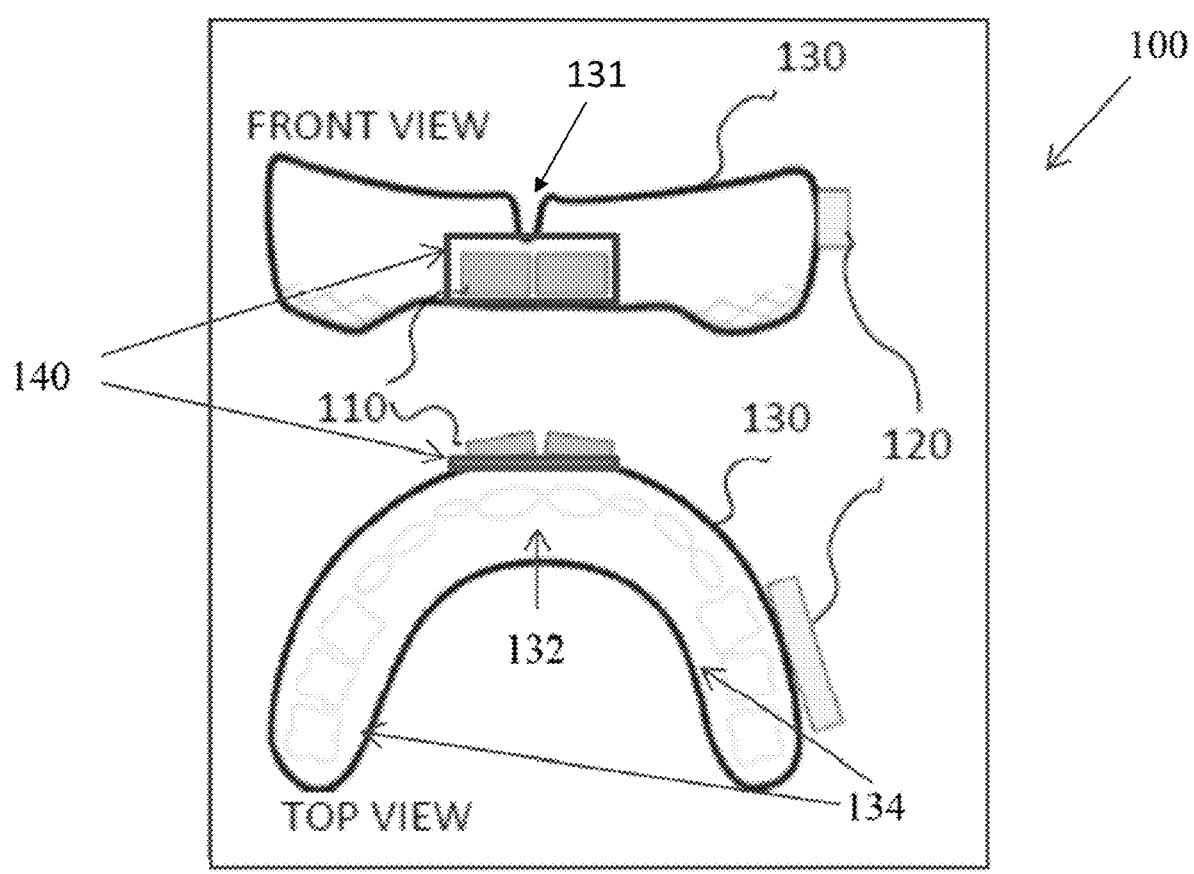
FIG. 1A: Oral appliance implemented as a mouthguard according to some embodiments.

FIG. 1A illustrates an oral appliance implemented as a mouthguard 100 according to some embodiments. By way of overview, the mouthguard 100 has the ability to collect high accuracy head impact measurements. The mouthguard 100 is implemented to couple rigidly to the skull through the upper teeth or through the palate, providing for improved measurement accuracy, and further providing an ability to instrument un-helmeted athletes. Features of the mouthguard 100 include: 1) motion sensors 110 are isolated from sources of error that can introduce noise; 2) the sensors 110 have high sampling rates for measuring head impact accelerations and velocities; and 3) a methodology for analyzing measurements can be included to differentiate between head impacts and spurious events, such as dropping the mouthguard 100. These features can provide highly accurate head impact acceleration and velocity measurements of both sub-concussive and concussive head impacts, to improve quality of research, detection and prevention.

In FIG. 1A, the mouthguard 100 is depicted in a front view and a top view. The mouthguard 100 includes a body 130, or a base member, which has a generally U-shaped form defining a channel to receive an upper row of teeth of a human subject. As shown in FIG. 1A, the body 130 includes a front portion 132 and a pair of rear portions 134 connected through the front portion 132. The front portion 132 is formed to accommodate an upper incisor area, and the rear portions 134 are formed to accommodate upper molar areas. The body 130 is formed of a biocompatible material, such as poly(ethylene vinyl acetate) or another biocompatible polymer. In some embodiments, the body 130 is sized to accommodate at least 6 teeth, at least 8 teeth, at least 10 teeth or at least 12 teeth of a human subject. In some embodiments, the body 130 is at least about 4 cm long or at least about 6 cm or 8 cm long. In some embodiments, the channel of the body 130 is at least about 0.4 cm, at least about 0.5 cm, at least about 0.6 cm, at least about 0.7 cm, or at least about 0.8 cm deep. In some embodiments, the body 130 is custom formed using subject-specific upper dentition impressions to achieve a tighter coupling of the body 130 to the upper dentition.

The sensors 110 are affixed to, housed in, or embedded in the body 130 of the mouthguard 100 next to, or in front of, the front portion 132 of the body 130 accommodating two upper center incisors. Although the two sensors 110 are shown in FIG. 1A, in other embodiments, less than or more than two sensors can be included. The sensors 110 are mounted to an electronic board 140, which is affixed to, housed in, or embedded in the body 130 of the mouthguard 100. Additional electronic components can be mounted to the electronic board 140, and can be connected to the sensors 110. As shown in FIG. 1A, a battery 120 is affixed to, housed in, or embedded in the body 130 of the mouthguard 100 next to, or in front of, one of the rear portions 134 of the body 130 accommodating the molar area of an upper dentition, and the battery 120 is connected to the electronic board 140. Although shown as being positioned on an outside surface of the body 130 (facing towards a cheek area), the battery 120 may instead be positioned on an interior surface of the body 130 (facing towards a tongue area). The sensors 110 and the battery 120 may be molded into the biocompatible material of the mouthguard 100.

The sensors 110 can be implemented for operation at high sampling rates greater than about 800 Hz, such as about 1 kHz or greater, about 2 kHz or greater, about 5 kHz or greater, about 8 kHz or greater, about 10 kHz or greater, or about 20 kHz or greater, thereby allowing for detection of fast and high magnitude motion events related to a head impact. Head impacts can be characterized by impulse accelerations that occur over a short duration, and thus a high data sampling rate is desired to capture head impact information. For example, an about 100 kHz sampling rate is used in cadaver drop tests to measure head impact accelerations and velocities, and measurements are then filtered to simulate slower sampling rates and identify a rate sufficient to accurately capture the impact information. It is determined that, to capture at least about 90% of a peak head impact rotational velocity value, gyroscope sampling rates should be about 1 kHz or greater for certain bare head impacts.

As shown in FIG. 1A, the body 130 is a monolithic structure having a greater thickness in the rear portions 134 of the body 130 accommodating molar areas of an upper dentition, and a reduced thickness in the front portion 132 of the body 130 accommodating an incisor area of the upper dentition. In such manner, the thicker rear portions 134 of the body 130 provide standoff regions that extend into a bite plane between molar areas of the upper dentition and molar areas of the lower dentition, with a gap or a recess 131 defined in the material of the body 130 between the two upper molar areas such that there is, in turn, a gap 131 between the sensors 110 and the bite plane at a front area of the mouth. For example, an extent of the gap 131 can be about 0.5 mm or greater, about 1 mm or greater, or about 2 mm or greater. This isolates potential jaw perturbances to the rear molars and away from the sensors 110 next to the incisors, to isolate the incisors from bite forces, and thereby isolate the sensors 110 from the bite forces.

Figure 1B:
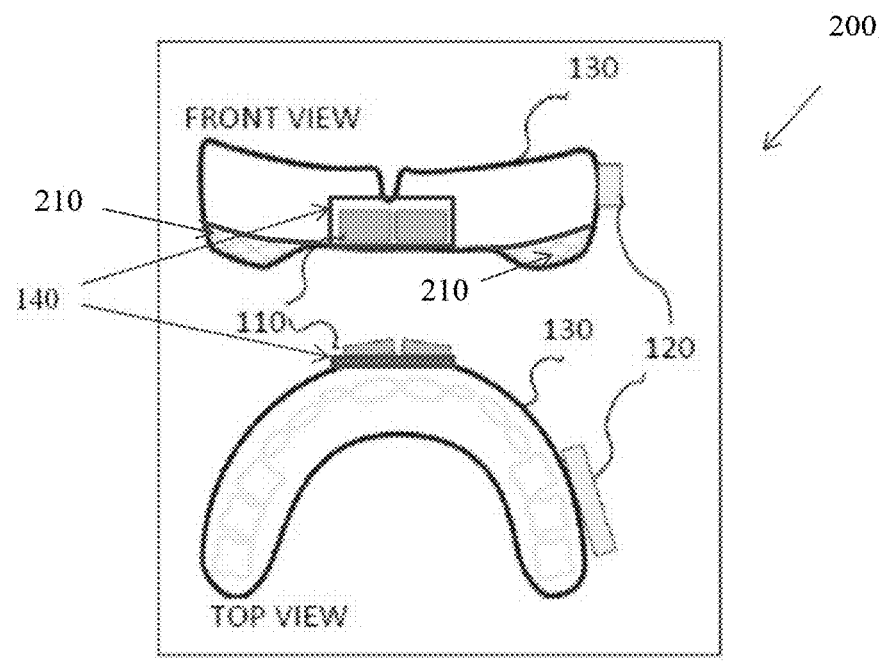
FIG. 1B: Oral appliance implemented as a mouthguard according to additional embodiments.

FIG. 1B illustrates an oral appliance implemented as a mouthguard 200 according to additional embodiments. Certain features of the mouthguard 200 are similarly implemented as explained for the mouthguard 100 of FIG. 1A, and details on those features are not repeated. As shown in FIG. 1B, in addition to sensors 110 next to an upper incisor area and a battery 120 next to an upper molar area, a body 130 of the mouthguard 200 includes standoff regions 210 that extend into a bite plane between molar areas of an upper dentition and molar areas of a lower dentition, with a gap or a recess defined in the body 130 between the two upper molar areas such that there is, in turn, a gap between the sensors 110 and the bite plane at a front area of the mouth. For example, an extent of the gap can be about 0.5 mm or greater, about 1 mm or greater, or about 2 mm or greater. This isolates potential jaw perturbances to the rear molars and away from the sensors 110 next to the incisors, to isolate the incisors from bite forces, and thereby isolate the sensors 110 from the bite forces.

In some embodiments, the body 130 is formed as two separate portions, where one portion of the body 130 includes a standoff material to provide the standoff regions 210, and another portion of the body 130 includes the sensors 110 and the battery 120 affixed thereto or embedded therein. The standoff material can be a biocompatible material, such as a biocompatible polymer, which may be the same as or different from a material of the remaining portion of the body 130. The standoff material can be, for example, an elastomer.

Figure 1C:
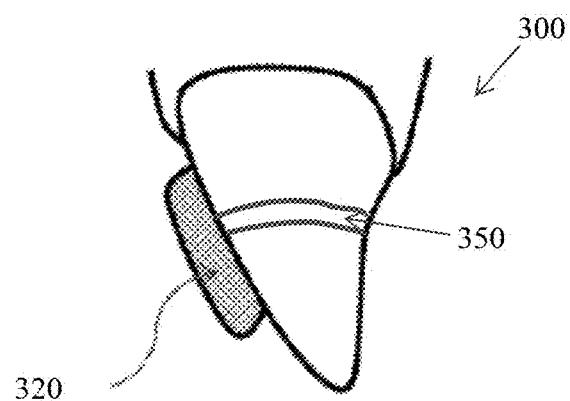
FIG. 1C: Oral appliance implemented as a tooth patch according to additional embodiments.

FIG. 1C illustrates an oral appliance implemented as a tooth patch 300 according to additional embodiments. Certain features of the tooth patch 300 are similarly implemented as explained for the mouthguard 100 of FIG. 1A, and details on those features are not repeated. As shown in FIG. 1C, the tooth patch 300 includes a body 320, which houses one or more sensors and a battery, and which is clipped to a single upper tooth by a fastening mechanism 350. The sensors and the battery may be mounted to an electronic board. In other embodiments, the sensors and the battery can be housed in respective bodies which are clipped to different teeth in an upper dentition. In other embodiments, a first sensor is clipped to one tooth and a second sensor is clipped to the same tooth or to a different tooth. In further embodiments, additionally or alternatively to the fastening mechanism 350, an adhesive may be used to affix the body 320 to an upper dentition.

Figure 1D:
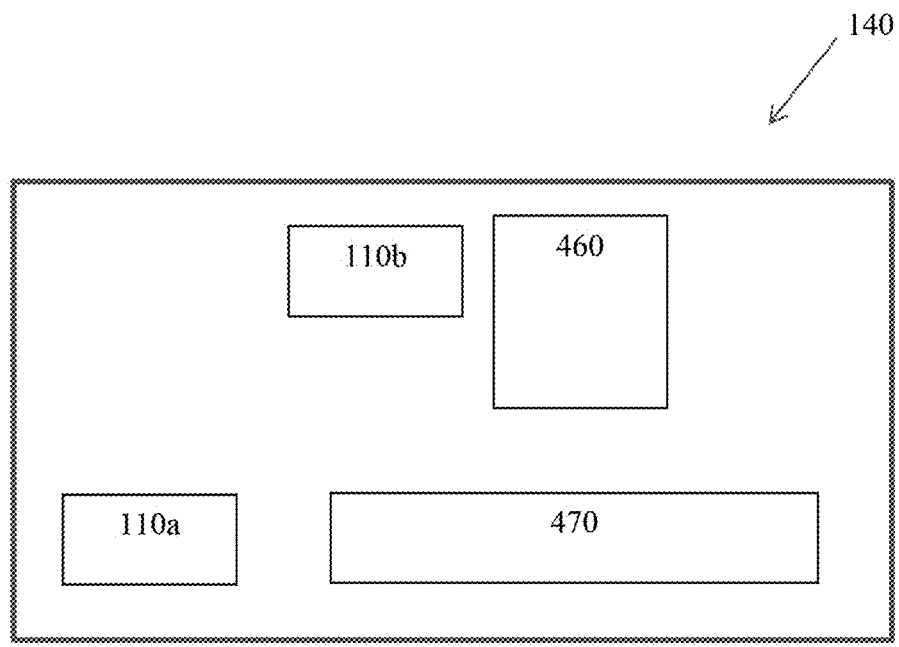
FIG. 1D: Electronic board and electronic components mounted to the electronic board according to some embodiments.

FIG. 1D illustrates the electronic board 140 and electronic components mounted to the electronic board 140 according to some embodiments. As shown in FIG. 1D, the electronic components include a first sensor 110a, which is a linear acceleration sensor such as an accelerometer, and a second sensor 110b, which is a rotational velocity sensor, such as a gyroscope. In some embodiments, the first sensor 110a is a multi-axial accelerometer, such as a tri-axial accelerometer or a dual-axial accelerometer. In some embodiments, the second sensor 110b is a multi-axial gyroscope, such as a dual-axial gyroscope or a tri-axial gyroscope. A processor 460, such as in the form of a microcontroller, is also mounted to the electronic board 140, and directs operation of the sensors 110a and 110b and collection of head motion data measured by the sensors 110a and 110b. Further, a wireless module 470 is mounted to the electronic board 140, and operates for wireless communication.

Figure 2:
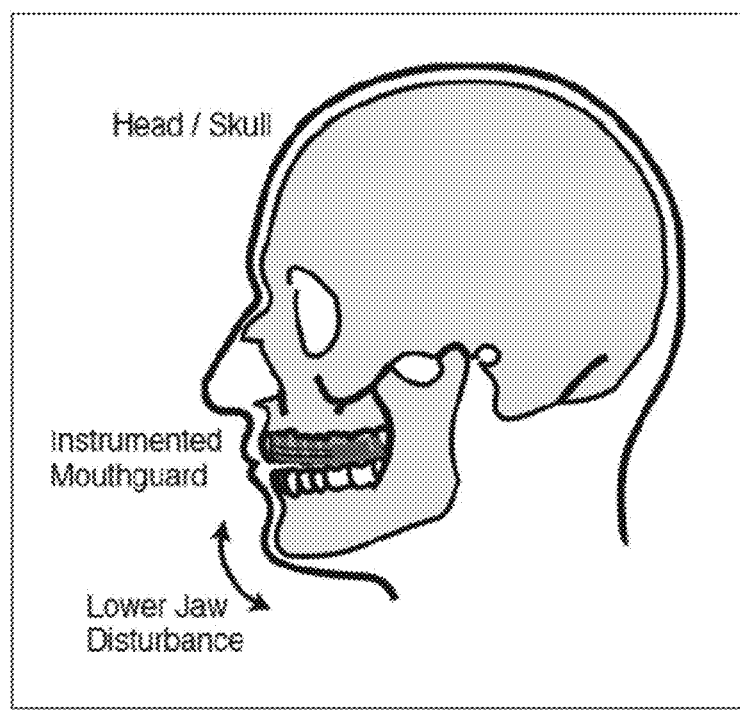
FIG. 2: Placement of an oral appliance implemented as a mouthguard over an upper dentition, according to some embodiments.

FIG. 2 illustrates placement of an oral appliance implemented as a mouthguard over an upper dentition, according to some embodiments. The mouthguard mitigates errors due to lower jaw perturbance by isolating sensors positioned next to incisors from bite forces.

In some embodiments, additionally or alternatively to isolating lower jaw perturbance from sensors, measurement data from sensors can be adjusted to reduce or remove contributions or noise from jaw perturbance. For example, in addition to sensors for kinematic measurements, an oral appliance can include one or more bite force sensors or strain gauges to measure contributions from jaw perturbance, and kinematic measurement data can be adjusted based on measured jaw perturbance.

It should be understood that an oral appliance may move for reasons other than mandible movement. For example, a person may move a mouthguard with tongue or lips, or the mouthguard may be moved by a force external to the person, such as by a boxer's punch, an opposing soccer player's elbow to the face, and so forth. The mouthguard of some embodiments isolates extraneous movement from movement of the skull. Isolation, as described above, may be through an addition of a standoff or suspension-type material as, for example, described with respect to FIG. 1B, or through formation or separation of the mouthguard such that sensors are less subject to extraneous motion of a portion of the mouthguard, or through signal processing techniques to remove contributions from extraneous motion.

Figure 3:
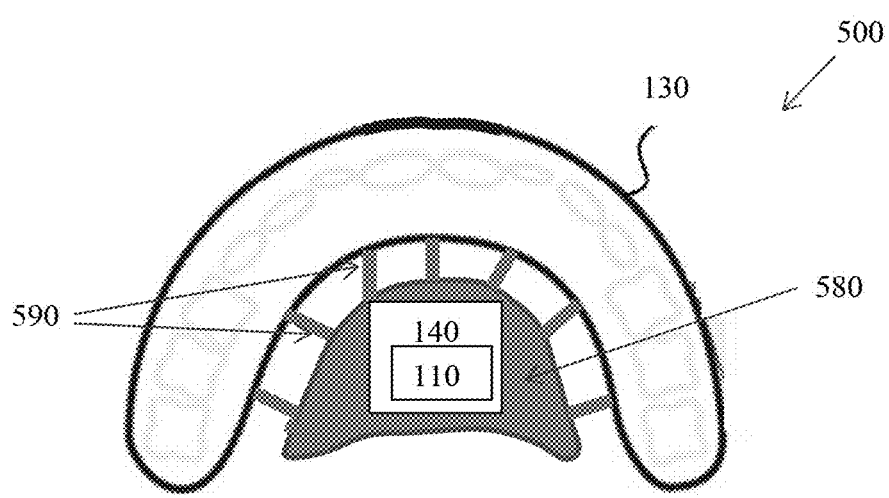
FIG. 3: Oral appliance implemented as a mouthguard according to additional embodiments.

Additional embodiments are contemplated to position motion sensors to isolate skull motion from extraneous motion. In some embodiments, one or more motion sensors are affixed to or positioned next to an area of an upper palate or gums rather than an upper dentition. FIG. 3 illustrates an oral appliance implemented as a mouthguard 500 according to additional embodiments. In addition to a body 130 to accommodate an upper dentition, the mouthguard 500 includes a retainer 580 to which an electronic board 140 including mounted sensors 110 are affixed thereto or are housed or embedded therein. The retainer 580 positions the sensors 110 next to an upper palate, with isolating struts 590 connecting the retainer 580 to the body 130 and providing isolation between the body 130 and the retainer 580. A series of apertures or cutouts between the struts 590 connecting the retainer 580 and the body 130 allow at least some extent of independent movement to isolate the sensors 110. To further improve isolation, a soft or thinned layer of a material may surround the sensors 110 such that the sensors 110 may remain fixed to the skull while other portions of the mouthguard 500 can move freely.

In some embodiments, an oral appliance can be used in combination with other sensors, such as an infrared reflectance sensor in a helmet or other headgear or a sensor affixed to the skin. Information from such other sensors may be used independently from, or in combination with, the oral appliance to identify, quantify and count impact occurrences. For example, learning data can be used to classify impact events according to occurrence, severity, or duration, and sensed data can then be analyzed to determine if a classification applies to an event.

In some embodiments, an oral appliance can implement a head impact detection technique to differentiate between head impacts and spurious non-impact events. Because wearable sensors are lightweight, the sensors can undergo high accelerations and exceed predefined impact thresholds when spurious events occur such as dropping a sensor on the ground. Spurious events can be misidentified as head impacts. The impact detection technique can use an infrared proximity sensor to determine if a mouthguard is in place on the teeth and a machine learning classifier that analyzes a frequency content of head impact and spurious event acceleration signals. Potential impacts are identified, off-teeth events are rejected, non-impact events are determined and rejected using the classifier, and remaining identified potential impacts are collected as head impact events. In some embodiments, potential impacts are identified when linear accelerations cross a certain threshold.

EXAMPLES

The following examples describe specific aspects of some embodiments of this disclosure to illustrate and provide a description for those of ordinary skill in the art. The examples should not be construed as limiting this disclosure, as the examples merely provide specific methodology useful in understanding and practicing some embodiments of this disclosure.

Example 1

Effect of the Mandible on Mouthguard Measurements of Head Kinematics

Overview:

Wearable sensors are becoming increasingly popular for measuring head motions and detecting head impacts. Many sensors are worn on the skin or in headgear and can suffer from motion artifacts introduced by the compliance of soft tissue or decoupling of headgear from the skull. An instrumented mouthguard is designed to couple directly to an upper dentition, which is made of hard enamel and anchored in a bony socket by stiff ligaments. This gives the mouthguard superior coupling to the skull compared with other systems. However, multiple validation studies have yielded conflicting results with respect to the mouthguard's head kinematics measurement accuracy. Here, this example demonstrates that imposing different constraints on the mandible (lower jaw) can alter mouthguard kinematic accuracy in dummy headform testing. In addition, post mortem human surrogate tests utilizing the worst-case unconstrained mandible condition yield about 40% and about 80% normalized root mean square error in angular velocity and angular acceleration respectively. These errors can be modeled using a spring-mass system in which the soft mouthguard material near the sensors acts as a spring and the mandible as a mass. However, the mouthguard can be designed to mitigate these disturbances by isolating sensors from mandible loads, improving accuracy to below about 15% normalized root mean square error in all kinematic measures. Thus, while other mouthguards can suffer from measurement errors in the worst-case unconstrained mandible condition, improved mouthguards should be designed to account for these disturbances and validation testing should include unconstrained mandibles to ensure proper accuracy.

Introduction:

Head motion sensors are designed to provide head impact kinematics measurements. However, various sensors suffer from a lack of sufficient coupling to the skull. For example, clothing/equipment sensors can move with respect to the skull during impact and skin-mounted sensors are prone to errors resulting from soft tissue motion. An instrumented mouthguard is a design that couples to the upper dentition—an exposed hard surface anchored in a bony socket of the maxilla by stiff ligaments. This allows the mouthguard to directly measure skull kinematics rather than the motion of an intermediate medium. While the upper dentition can move under high loads, other dynamic mobility tests have shown that teeth mobility has a peak amplitude on the sub-millimeter scale in an oscillatory excitation range of about 3000-4000 Hz. This frequency is above that for typical head impacts and beyond the sensing capabilities of wearable microelectromechanical (MEM) devices. The tooth motion is also smaller than skin or clothing/equipment motion, which can be on a centimeter scale.

The finding that direct coupling to the upper dentition provides for improved accuracy of impact measurement derived from an inquiry as to why different test results were achieved between different tests of an in-mouth appliance, when each test was performed on an anthropomorphic test dummy (ATD). After investigating this topic, it was determined that a possible cause was that each study used a different constraint on the mandible (lower jaw). One study preloaded the mandible onto the in-mouth appliance, creating a "clench" to keep the appliance in place; another study used an articulating mandible that was loosely held in place with springs; and another study omitted the mandible from the ATD.

Because the mandible directly contacts the mouthguard through the lower dentition, mandible motion could cause deformations within the mouthguard when the upper dentition and lower mandible close during a dynamic event. Thus, it is hypothesized that the mouthguard kinematic measurement accuracy depends on the mandible constraint during an impact. It is hypothesized that an unconstrained mandible (slack jaw) articulates during an impact and interacts with the mouthguard, potentially causing kinematic measurement errors. A mandible that is removed or tightly clenched will reduce mandible motion and measurement error. While ATD testing is useful for understanding the underlying interaction between the mandible and the mouthguard, the ATD mandible makes simplifications of human anatomy. Thus, a post mortem human surrogate (PMHS) test is performed with an unconstrained mandible to assess mouthguard accuracy in a biofidelic worst-case field scenario.

Materials and Methods:

To test the hypothesis and evaluate the mandible constraint's effect on mouthguard kinematic measurement accuracy, free fall drop experiments are performed on football helmeted ATD and PMHS heads over a range of impact locations and heights while varying the mandible constraint.

Instrumentation

Instrumented Mouthguard

Figure 4:
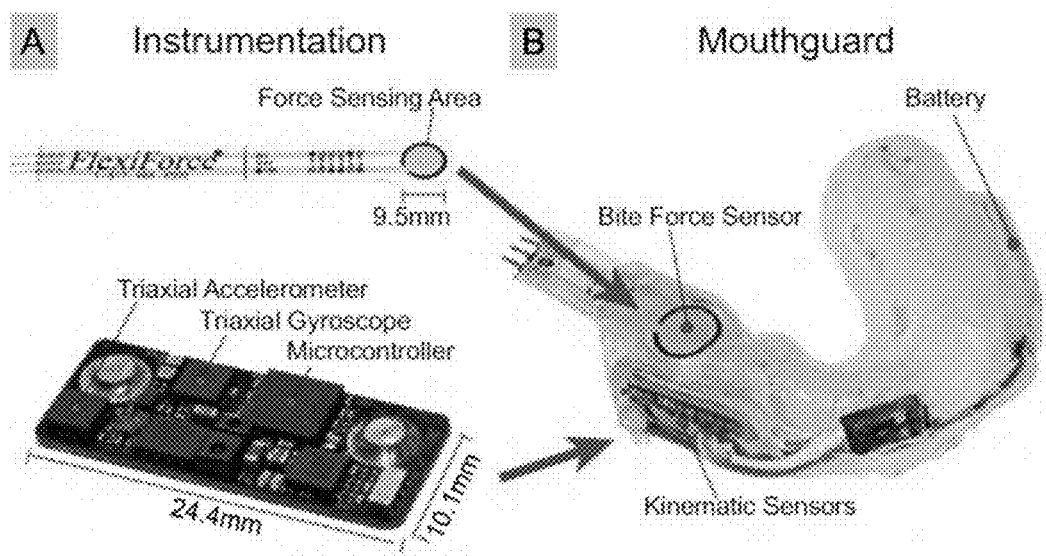
FIG. 4: Instrumented Mouthguard. (A) The instrumented mouthguard includes a bite force sensor and a kinematics sensor board with a tri-axial accelerometer and a tri-axial gyroscope. (B) The kinematic sensor board is embedded in layers of ethylene vinyl acetate (EVA) that are pressure formed around custom made dentition molds.

The instrumented mouthguard was formed using molds of the ATD and PMHS dentitions (FIG. 4). The distance between the center of the two rear molars in both the ATD and PMHS were measured to assess the size of the mouthguards (Table 1). Two layers of about 3 mm ethylene vinyl acetate (EVA, Great Lakes 032-021) were pressure formed around a kinematic sensing board and battery encapsulated in hard plastic. The sensor board included a tri-axial gyroscope (ITG3500A) and a tri-axial accelerometer (H3LIS331DL) which both sampled data at about 1000 Hz over a period of about 100 ms with about 10 ms pre-impact trigger. Data recording was triggered when linear acceleration magnitude reached about 10 g. Finally, a force sensor (Flexiforce A201) was placed above the sensing board in the bite plane and measured bite force between impact trials.

TABLE 1

Experimental Properties. The mass properties for the ATD, PMHS heads, and helmets. In addition, helmet size and dentition size are measured for the ATD and PMHS heads used in this example.

| Head | Head mass | Head circumference | Helmet size | Helmet mass | Mouthguard width |
|---|---|---|---|---|---|
| ATD | 4.0 kg | 54.6 cm | Medium | 1.7 kg | 5.04 cm |
| PMHS D3 | 3.4 kg | 55.2 cm | Large | 2.2 kg | 4.73 cm |
| PMHS D4 | 4.5 kg | 59.0 cm | Extra large | 2.3 kg | 4.46 cm |
| PMHS D5 | 3.6 kg | 58.0 cm | Large | 2.2 kg | 5.13 cm |

ATD Reference Sensors

Figure 5:
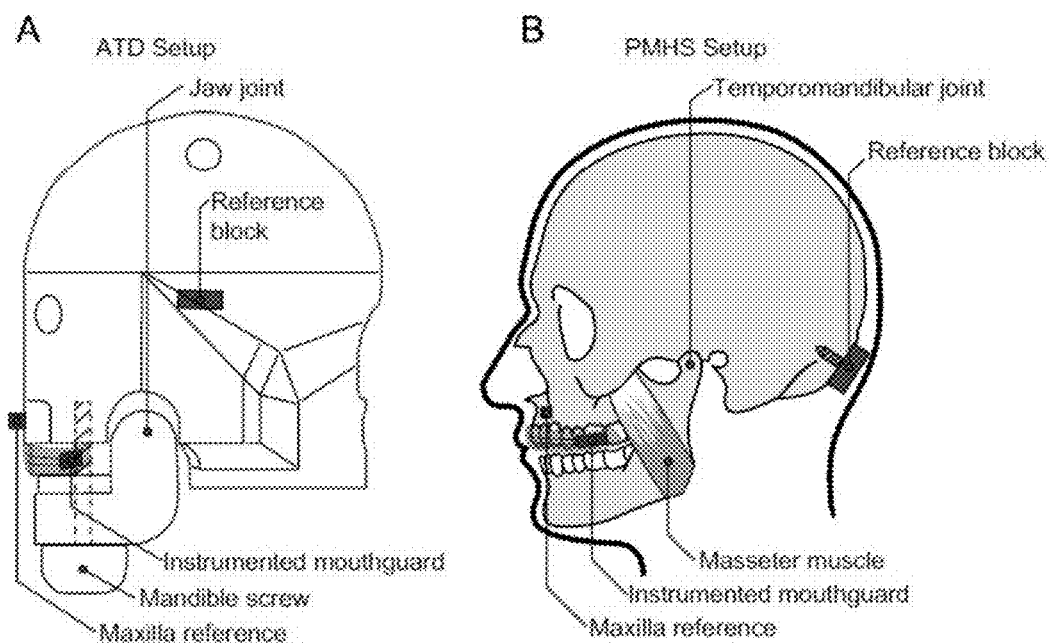
FIG. 5: Experimental Setup. (A) Anthropomorphic test dummy (ATD) and (B) post mortem human surrogate (PMHS) sensor setup for experiments. Both the ATD and PMHS were equipped with mouthguards along with rigidly affixed maxilla sensors and reference sensor blocks.

Both the ATD and PMHS heads were equipped with a rigidly affixed reference kinematic sensor and maxilla kinematic sensor (FIG. 5). The reference sensor was used to assess mouthguard accuracy while the maxilla sensor was used to ensure skull rigidity.

A modified X2 headform (X2 biosystems, Seattle Wash.) was used without the neck as the ATD. The ATD had the inertial properties of a 50th percentile male head (Table 1). The ATD reference sensor was comprised of a tri-axial accelerometer (Dytran 3237A1) at the center of mass and a tri-axial gyroscope (ARS-PRO-18K) aligned with anatomical coordinates. These sensors recorded data at about 10 kHz over a period of about one second during an impact. An about 10 g linear acceleration magnitude trigger was used without fixed pre-impact or post-impact timings. The ATD maxilla sensor had the same specifications and protocols as the instrumented mouthguard. Finally, the mandible of the ATD is also instrumented with a kinematic sensor using the same specifications and protocols as the instrumented mouthguard to measure mandible dynamics.

PMHS Reference Sensors

Three male PMHS heads are obtained for testing, each disarticulated at the atlanto-occipital joint (Table 1). The PMHS reference kinematic sensor had a 6-degree-of-freedom block (Endevco 7624C-2000 and ARS-PRO-8K) affixed to the occiput collecting data at about 100 kHz over a period of about 600 ms with an about 100 ms pre-impact trigger. Impacts were triggered when a vertical force of about 78.1 N was registered by an about 100 kHz tri-axial force plate, upon which the PMHS were dropped. The PMHS maxilla sensor included a pair of tri-axial accelerometers placed on the left and right sides of the maxilla, each measuring data at about 10 kHz over a period of about 380 ms with about 20 ms pre-impact trigger. Maxilla impact trigger occurred when linear acceleration magnitude reached about 10 g.

Testing Protocol

In preparation for a drop trial, the mandible constraint is first adjusted to one of three conditions: no mandible, unconstrained mandible, and clenched mandible. In the ATD, all three mandible constraints are tested to assess how mandible constraint affected mouthguard accuracy, and to understand the underlying interaction between the mandible and mouthguard. In PMHS, the unconstrained mandible condition was tested to assess mouthguard accuracy in a representative biofidelic worst-case field scenario. In the no mandible condition, the ATD mandible is removed entirely. In the unconstrained mandible condition, the ATD and PMHS mandibles were allowed to articulate freely. Finally, to achieve the clenched mandible condition, the ATD mandible is used to apply an about 300 N (about 4.2 MPa) preload to the mouthguard. A typical adult male peak bite force at the rear molar is 294±56 N.

In the ATD, the mandible had a single degree-of-freedom pivot representing the temporomandibular joint. The ATD mandible was removed at this joint to satisfy the no mandible condition. A large screw threaded through the bottom of the mandible into the maxilla (FIG. 5) was tightened or loosened for remaining mandible conditions. In a loosened state, the mandible was free to articulate (unconstrained) while in a tightened state, there was an about 300 N load on the rear molar (clenched).

Figure 6:
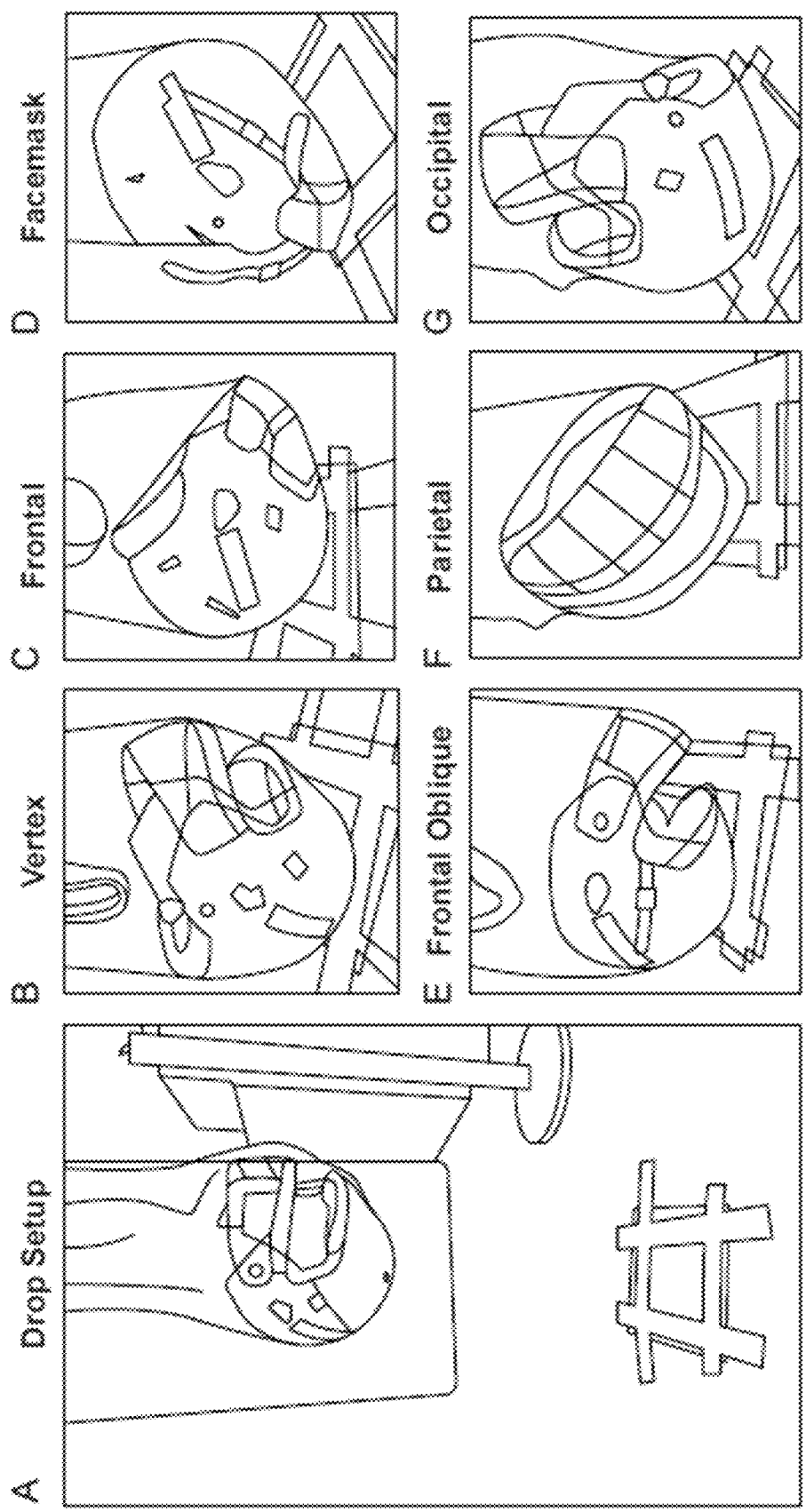
FIG. 6: Impact Locations. (A) A free drop setup is used over three drop heights of about 10 cm, about 60 cm, and about 100 cm. (B)-(G) Six impact orientations are tested to simulate impacts commonly seen in football.

With the mandible set, the ATD or PMHS is placed into a Riddell Speed Helmet (Riddell, Rosemont Ill.) and the helmeted system is loaded into a net. The Riddell Speed helmet size is selected based on the ATD or PMHS head circumference (Table 1). The net is suspended to one of three heights: about 10 cm, about 60 cm, and about 100 cm, which yielded impacts ranging from about 15 g-150 g. The ATD or PMHS heads were then oriented to impact on one of six locations: vertex, frontal, facemask, frontal oblique, parietal, and occipital (FIG. 6). This range of severities and locations encompassed those most common in football. The net is released and the ATD or PMHS is allowed to free fall onto an aluminum plate. Each test condition is repeated thrice for the ATD and twice for each PMHS.

Analysis

Data Processing

Raw signals are filtered using a fourth-order Butterworth low-pass filter according to Society of Automotive Engineers (SAE) protocols. An about 300 Hz low-pass cutoff frequency was used for the linear acceleration signals and about 184 Hz was used for the angular velocity signals that were collected by the mouthguard, ATD maxilla, and ATD mandible. These cutoff values were determined by the sensors' specified maximum bandwidths. For all other sensors, CFC1000 (about 1650 Hz) was used for linear acceleration signals and CFC180 (about 300 Hz) was used for angular velocity signals. Angular accelerations were determined by differentiating the angular velocity signals using a 5-point stencil.

Kinematic signals are transformed to the head center of mass to assess mouthguard accuracy and to the mouthguard sensor board location to identify how the mouthguard decouples from the upper dentition. Kinematics at the head center of mass are used to calculate injury criteria on the field; however, kinematics at the mouthguard location can be used to assess mouthguard coupling, where the reference measurements represent the upper dentition motion and a discrepancy in the mouthguard measurement represents mouthguard decoupling.

Sensors and head center of mass locations and orientations for the ATD were determined using a CAD model. Micro-CT scans (Nikon XTH 225 ST) were used to identify these values for the PMHS heads. The sub-millimeter size of the electronic chips in the mouthguard and maxilla sensors specified the increased resolution of the micro-CT scan. The PMHS center of mass was identified using landmarks found in the micro-CT scans.

Reference Verification

Verification of transformed reference data is performed by comparing the reference and maxilla sensor linear accelerations. Since both sensors were affixed directly to the skull and the skull was assumed to be rigid, both sensors should have measured the same motion if the head acted as a rigid body. Thus, exclusion was made of impacts with normalized root mean square (NRMS, normalized by the peak value) error between the reference and maxilla linear acceleration magnitude exceeding about 20%.

Accuracy Evaluation

Assessment of mouthguard accuracy is performed by comparing the reference and mouthguard peak angular velocity magnitude, peak angular acceleration magnitude, and peak linear acceleration magnitude measured at the ATD head center of mass. Peaks from all impacts are compiled for a mandible condition in the ATD and a linear regression is performed forcing the y-intercept to zero.

To determine the similarity of PMHS and ATD results, computation is performed of the NRMS error between the mouthguard and reference sensors for the head center of mass angular velocity magnitude, angular acceleration magnitude, and linear acceleration magnitude. A two-sided t-test is used to compare the PMHS unconstrained mandible condition errors against the ATD unconstrained mandible condition errors.

Since it is hypothesized that the mandible affects mouthguard accuracy, substantial kinematic errors in certain testing conditions should be observed. To evaluate how the mouthguard decouples from the upper dentition and how the mandible interacts with the mouthguard, evaluation is performed of differences between the mouthguard and reference kinematics at the mouthguard sensor location. Signals are compiled with greater than about 20% NRMS error between the mouthguard and reference and the mouthguard error is computed by performing a point subtraction between the reference kinematics and the mouthguard kinematics. Identification is performed of characteristic noise frequencies using a Fourier analysis on the error signal.

Material Modeling

To further explore the interaction between the mandible and mouthguard, characterization is performed of the two components involved: the mandible and the mouthguard. The mandible is treated as a rigid body; however, the mouthguard was constructed using soft EVA and its material properties had not been previously characterized in compression. An Instron 5565 is used to estimate the mouthguard EVA material compressive modulus by applying 10 compression-decompression cycles between 0% and about 25% strain at a constant strain rate of about 30%/min. The maximum strain was near the load cell's about 100 N limit (about 1.4 MPa). In addition, with a typical impact of about 100 g acceleration and a mass of about 0.45 kg, the mandible can exert an about 450 N load shared between the temporomandibular joint and mouthguard. The about 225 N mouthguard load, spread over the bite plane (about 5 cm$^2$) results in an about 0.45 MPa pressure, which falls within the material testing limits.

Figure 7:
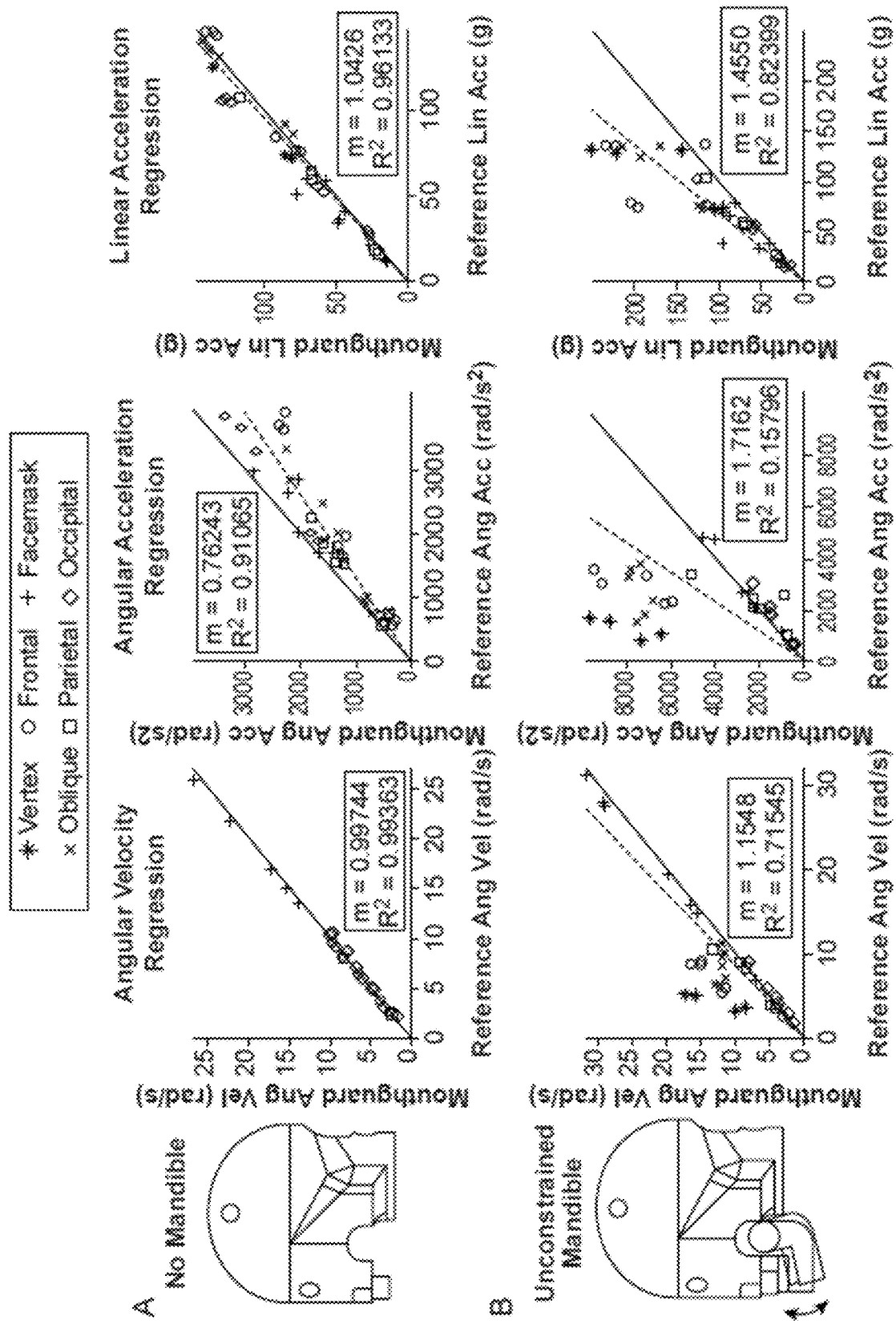
FIG. 7: ATD Results at Head Center of Mass. (A) In the no mandible case, the mandible was removed and the mouthguard shows good accuracy in angular velocity and linear acceleration with a consistent about 20% underestimation in angular acceleration at the center of mass. (B) In the unconstrained case, the mandible was allowed to articulate freely and the mouthguard shows greater variance in angular velocity and severe over-estimation in angular acceleration. (C) In the clenched case, the mandible was closed and preloaded against the mouthguard and upper dentition. The mouthguard in this case shows results similar to the no mandible condition.
Figure 7:
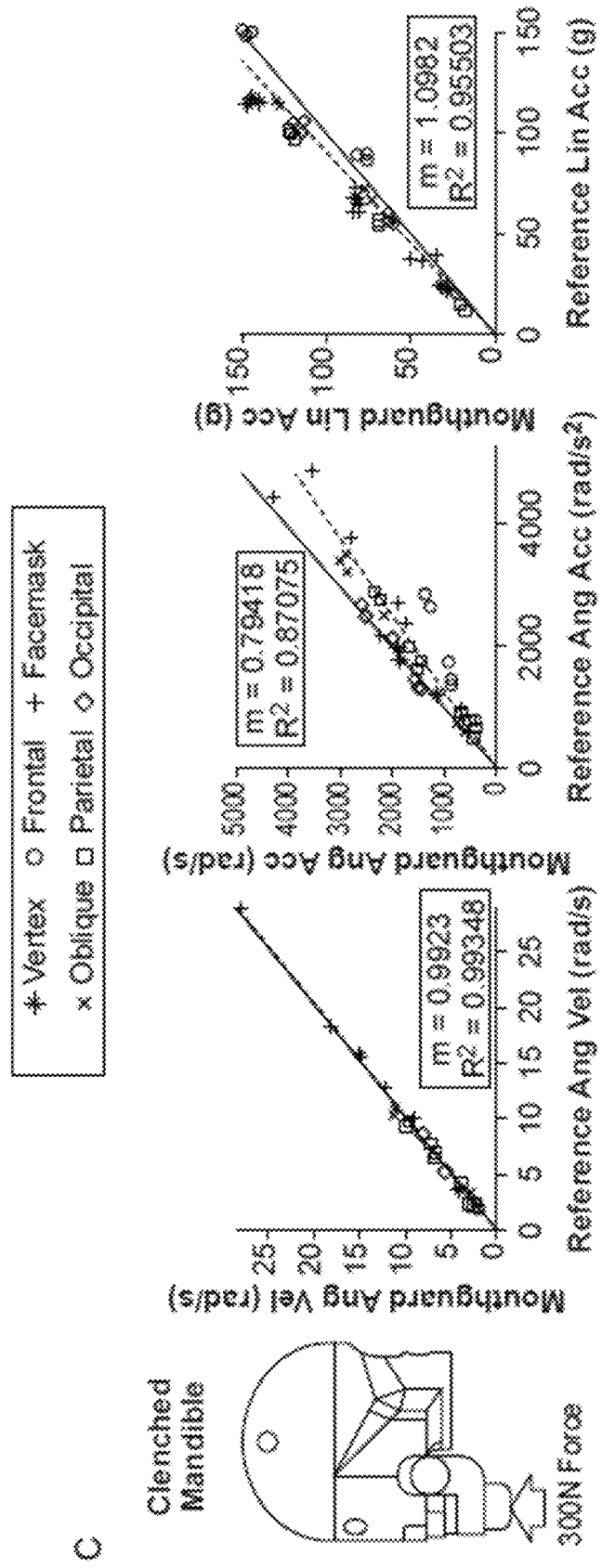

Results:

Mouthguard Accuracy 162 drops were conducted on the ATD, of which 8 had linear acceleration NRMS error greater than about 20% between the ATD reference and ATD maxilla sensor. The regression analysis in the ATD for the peak magnitude angular velocity, angular acceleration, and linear acceleration measured at the head center of mass are shown in FIG. 7. The no mandible and clenched mandible conditions have peak magnitude angular velocity and linear acceleration regression slopes near m=1 with $R^2$ close to 1, indicating good mouthguard accuracy. Peak magnitude angular acceleration regressions show that the mouthguard generally underestimated the reference sensor.

The unconstrained mandible condition shows that the mouthguard overestimated the peak magnitude angular acceleration and peak magnitude linear acceleration significantly with m>1 and $R^2$<1. The regression for peak magnitude angular velocity also shows greater variance and slight overestimation (about 5%-10%). Location specific regressions for each mandible condition (Table 2) show that mouthguard accuracy is also location dependent. In the unconstrained mandible condition, impacts towards the top of the head (vertex, frontal, and frontal oblique) have the greatest overestimates in angular velocity and angular acceleration. In the no mandible and clenched mandible conditions, the frontal condition had the most underestimation in angular acceleration while the occipital condition had the least.

EVA Material Model

Figure 10:
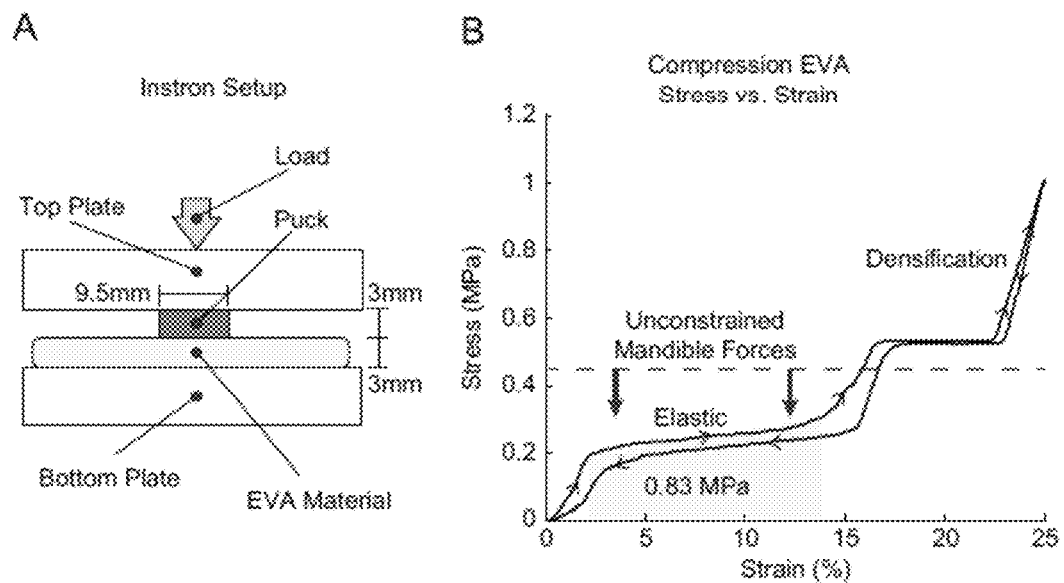
FIG. 10: EVA Material. (A) Using an Instron 5565, compression of a sample of EVA is performed to obtain the resulting stress-strain plot. (B) The compressive modulus from the elastic region represents the mandible inertial loading on the mouthguard during unconstrained jaw impacts and is used to predict how the EVA and mandible might interact.

The stress-strain plot for the mouthguard EVA material (FIG. 10) exhibits several linear elastic regions along with a substantially constant stress of about 0.6 MPa between about 17% and about 22% strain. The largest linear elastic region for the maximum unconstrained mandible pressure (about 0.45 MPa) occurs between about 2% and about 14% strain, resulting in an about 0.83 MPa compressive modulus.

TABLE 2

Location Dependence. A linear regression is performed at the center of mass for each impact location for each mandible condition in the ATD. In the unconstrained case, the vertex, frontal, and frontal oblique impact locations have significant overestimates in angular velocity and angular acceleration compared with the remaining impact locations.

| | | Vertex | | Frontal | | Facemask | | Frontal oblique | | Parietal | | Occipital | |
|---|---|---|---|---|---|---|---|---|---|---|---|---|---|
| | | m | $R^2$ | m | $R^2$ | m | $R^2$ | m | $R^2$ | m | $R^2$ | m | $R^2$ |
| No Mandible | Angular velocity | 0.8765 | 0.8416 | 1.0197 | 0.9975 | 1.0195 | 0.9993 | 0.9130 | 0.8938 | 0.9920 | 0.9930 | 0.9498 | 0.9943 |
| | Angular acceleration | 0.7588 | 0.6230 | 0.6252 | 0.9747 | 0.8640 | 0.9135 | 0.7211 | 0.9209 | 0.8083 | 0.9877 | 0.8537 | 0.9947 |
| | Linear acceleration | 1.1109 | 0.9953 | 0.9555 | 0.9883 | 1.2195 | 0.8480 | 0.9880 | 0.9893 | 1.0833 | 0.9973 | 1.1721 | 0.9977 |
| Unconstrained mandible | Angular velocity | 2.7373 | 0.6523 | 1.7958 | 0.9235 | 1.0325 | 0.9994 | 1.2753 | 0.7044 | 1.0956 | 0.9310 | 0.8653 | 0.9909 |
| | Angular acceleration | 5.2567 | 0.6134 | 2.5182 | 0.9083 | 0.8938 | 0.9800 | 2.3749 | 0.6385 | 1.0063 | 0.5646 | 0.7493 | 0.9873 |
| | Linear acceleration | 0.8765 | 0.8684 | 1.5789 | 0.6215 | 1.3023 | 0.6335 | 1.4935 | 0.9671 | 1.1657 | 0.9850 | 1.1477 | 0.9707 |
| Clenched mandible | Angular velocity | 1.0570 | 0.9902 | 1.0011 | 0.9786 | 0.9735 | 0.9983 | 1.0123 | 0.9800 | 1.0151 | 0.9776 | 1.0161 | 0.9753 |
| | Angular acceleration | 0.9357 | 0.9897 | 0.4887 | 0.9209 | 0.7945 | 0.9306 | 0.8544 | 0.9895 | 0.8003 | 0.9821 | 0.9625 | 0.9673 |
| | Linear acceleration | 1.2299 | 0.9965 | 0.9520 | 0.9848 | 1.2190 | 0.9387 | 1.1020 | 0.9975 | 1.2086 | 0.9970 | 1.1012 | 0.9972 |

Figure 8:
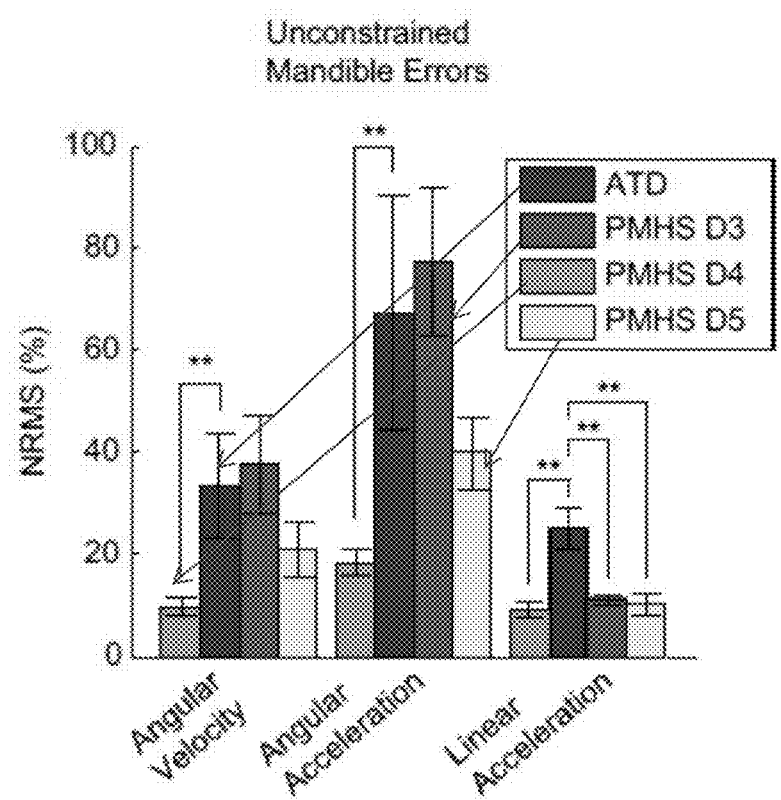
FIG. 8: PMHS Results at Head Center of Mass. Normalized root mean square (NRMS) comparison of center of mass kinematics between the ATD and the three PMHS heads. A two-sided t-test is used to compare PMHS NRMS errors against the ATD NRMS errors in the unconstrained mandible case. * indicates a $p<0.05$ significance and ** indicates a $p<0.01$ significance. The results show that the PMHS D3 and D5 errors are similar to the ATD; however the PMHS D4 errors are significantly lower.

108 drops were conducted over the three PMHS heads, of which 26 had a linear acceleration NRMS error greater than about 20% between the PMHS reference and PMHS maxilla sensor. The PMHS NRMS errors at the head center of mass were compared against the ATD NRMS errors at the head center of mass to assess if similar mandible effects were observed in the worst-case biofidelic environment (FIG. 8). This analysis shows that PMHS D3 and D5 had similar errors compared with ATD trials using the unconstrained mandible condition; however, PMHS D4 had significantly lower errors. Further analysis indicates that the PMHS D4 unconstrained mandible errors were similar to errors from ATD no mandible and clenched mandible conditions.

Figure 9:
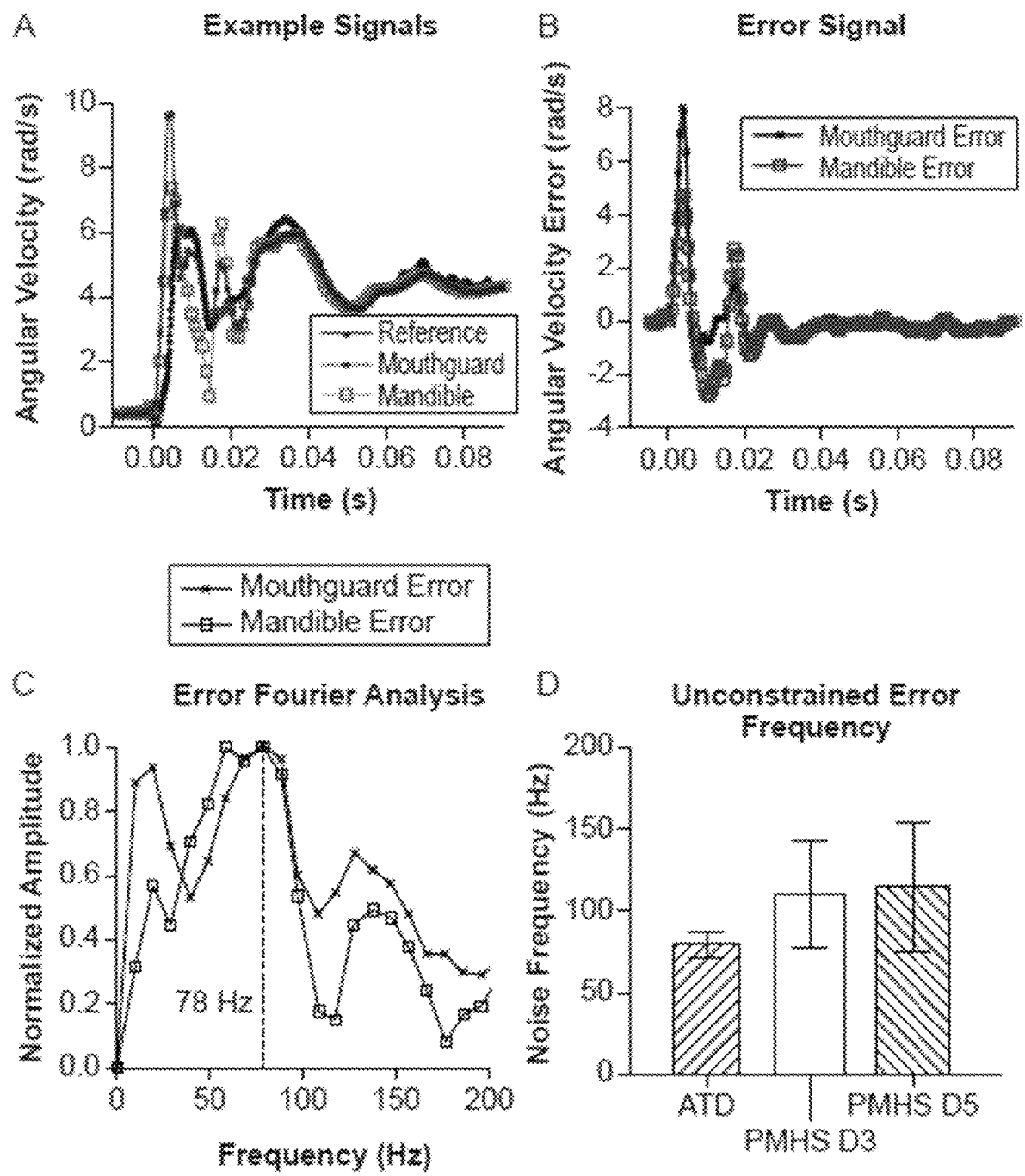
FIG. 9: Error Analysis at Mouthguard. (A) An example trace from an ATD unconstrained mandible drop trial shows that the mouthguard and ATD mandible sensor differ from the ATD reference at the mouthguard location. (B) Calculation is performed of the error between the mouthguard and ATD reference as well as the ATD mandible sensor and ATD reference. (C) A frequency analysis is performed on the error signals to identify a characteristic error frequency. (D) The characteristic error frequencies for the mouthguard are then averaged over all trials for the ATD and PMHS D3 and D5, showing that there is a consistent high frequency error in these unconstrained trials (D).

Angular velocity signals from 23 of 49 unconstrained mandible ATD drops had substantial error between the mouthguard and reference sensor (NRMS>about 20%) at the mouthguard sensor location. For the PMHS heads, all but one of the D3 and D5 drops had substantial error between the mouthguard and reference sensors in the angular velocity signal at the mouthguard sensor location. No D4 drops had substantial error in any kinematic signals at the mouthguard sensor location. Analysis is performed of mouthguard error signals for drops in both ATD and PMHS with NRMS>about 20% and the mean and standard deviation for the error signal peak frequencies are shown in FIG. 9. There were no substantial errors in the linear acceleration signals.

Finally, comparison is performed of the kinematics from the ATD reference, the mouthguard, and the ATD mandible. An example trace (FIG. 9) demonstrates that the mouthguard and mandible have similar kinematics. In the unconstrained mandible condition, there were additional lower mandible dynamics during the impact that resulted in measured kinematic errors in both the mandible and mouthguard. The frequency spectra of the dynamics in the mouthguard and mandible had similar shapes that were consistent between ATD or PMHS trials.

Discussion:

The results from the ATD testing support the hypothesis that the mouthguard kinematic measurement accuracy depends on the mandible constraint. The ATD unconstrained mandible condition shows poor mouthguard accuracy in angular acceleration. Regressions at each impact location indicate that impacts to the top of the head (vertex, frontal, and frontal oblique) result in higher overestimation (Table 2). This is likely due to the acceleration vector being closely aligned with the vector normal to the bite plane and the direction with the greatest mandible motion. Thus, impacts in these locations may yield greater mandible motion and larger inertial loading on the mouthguard.

The poor accuracy in the unconstrained mandible condition is again seen in two of three PMHS heads tested, which indicates that similar mandible dynamics could be present in worst-case mandible loading scenarios. Agreement between ATD and PMHS results implies that the ATD, despite being a simplification of human anatomy, is a reasonable model system for mouthguard validation studies. However, one PMHS head (D4) had good mouthguard accuracy in angular velocity and angular acceleration, comparable to the mouthguard accuracy in the ATD no mandible and clenched mandible conditions. One possible cause for the improved mouthguard accuracy is that the D4 PMHS had the smallest dentition (Table 2), which increased the thickness of the resulting mouthguard and dampened the mandible dynamics. It is also possible that contact with the lower dentition and mandible was not evenly distributed and that the sensor location received less impact loading and deformation in the D4 surrogate because the mouthguard is customized to the upper dentition and not the lower dentition. Higher static mandible muscle forces could bring more uniform loading on the lower dentition and mouthguard.

While the unconstrained mandible yielded poor mouthguard accuracy, this condition may represent an upper bound for expected errors on the field. Mandible muscles in vivo generally remain active to keep the mouth closed, whereas the mandible in the ATD and PMHS tests were supported by passive structures such as the chinstrap or soft tissue. Thus, as mandible muscle involvement increases, mouthguard accuracy may improve and approach the clenched mandible condition as the initial bite force increases and the mandible is further constrained. However, jaw muscle and bite forces during impacts remain to be ascertained.

Figure 11:
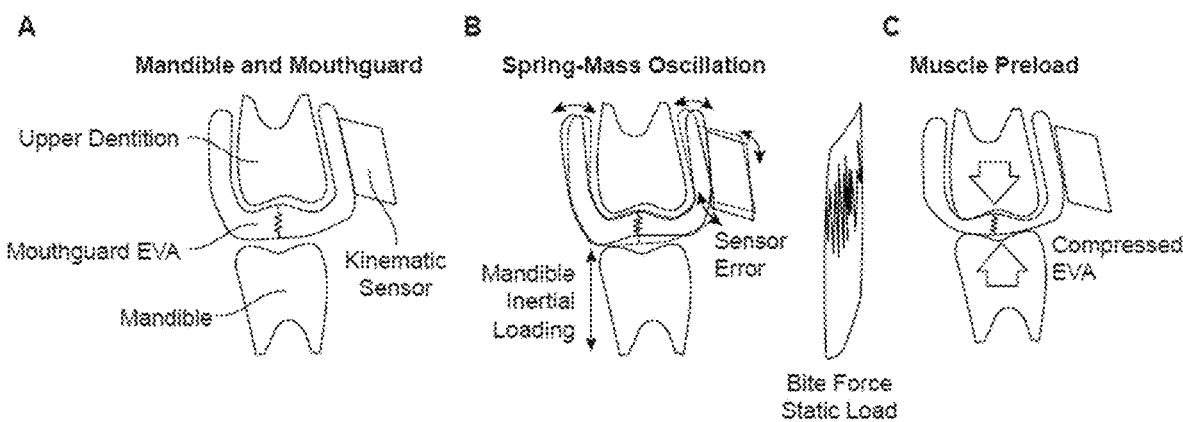
FIG. 11: Mandible Dynamics and the Mouthguard. (A) The mandible dynamics can be modeled as a spring-mass system in which the mandible/dentition are the mass and the EVA is the spring. (B) An impact forces the system to oscillate, resulting in a characteristic frequency disturbance in the mouthguard. (C) The mandible dynamics can be mitigated through the use of the jaw muscles to preload the mouthguard.

Having identified that the mandible constraint can affect mouthguard measurements, an explanation is made of a potential mechanism underlying the errors. The lack of linear acceleration errors at the mouthguard sensor board indicates that the mouthguard does not fully decouple from the upper dentition. One possible cause of the disturbances is the vibration of the mandible against the mouthguard, which can be modeled as a second-order spring-mass system. In this model, the mouthguard EVA material acts as the spring and the mandible acts as the mass (FIG. 11). Using the EVA compressive modulus (about 0.83 MPa), the bite plane surface area (about 5 $cm^2$), and the EVA thickness (about 3 mm), it is determined that the mouthguard acts as a spring with a stiffness of about 140 kN/m. Combined with the mass of the ATD mandible (about 0.45 kg), this gives a natural frequency of about 88.4 Hz, which closely matches the ATD unconstrained error frequency of about 86.6 Hz (FIG. 9). Dynamic loading of the mandible on the mouthguard has been observed in other ATD tests, with about 50N-300 N loads in the upper dentition occurring at about 10 ms intervals (about 100 Hz). When high frequency gyroscope noise signals are differentiated to obtain angular acceleration, these can amplify to result in large overestimates (FIG. 7).

Figure 12:
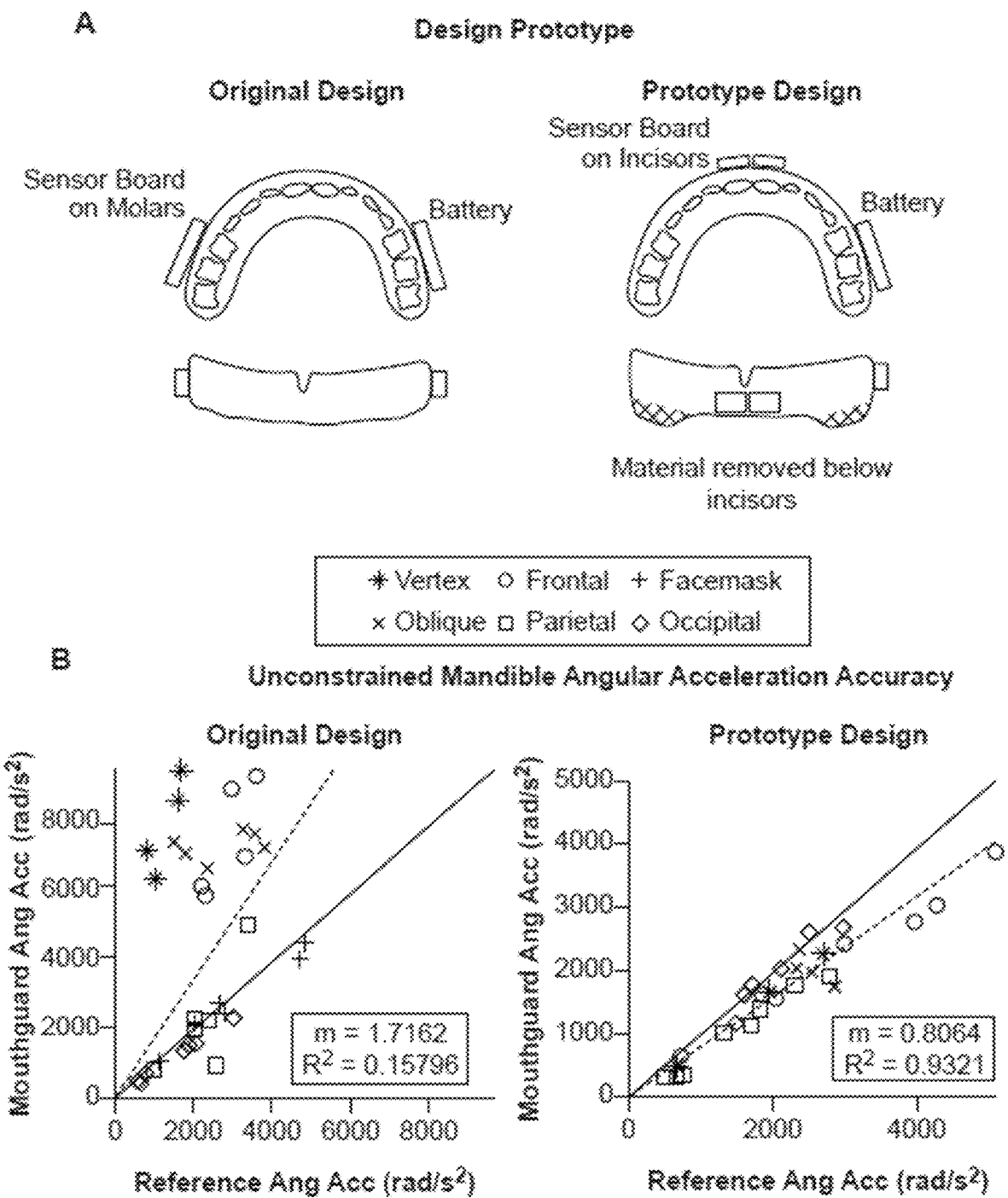
FIG. 12: Disturbance Isolation Mouthguard Design. (A) The mouthguard can be designed to mitigate the effect of the mandible dynamics by placing the kinematic sensors in front of the incisors and removing EVA material in the bite plane below the incisors. As a result, the mandible is supported by the mouthguard at the molars while the kinematic sensors are isolated at the incisors. (B) Results from ATD drop tests with an unconstrained mandible show improved accuracy in angular acceleration with this improved design compared with the original design.

To further support this model, a prototype mouthguard is developed with kinematic sensors in front of the incisors and EVA material removed from the bite plane at the incisors (FIG. 12). This effectively separates the portion of the mouthguard supporting the mandible at the rear molars from the portion of the mouthguard housing the kinematic sensors at the incisors. Repeating the ATD free fall drops using the prototype mouthguard in the worst-case unconstrained mandible condition resulted in mouthguard accuracy similar to the ATD no mandible and clenched mandible conditions (FIG. 12). NRMS errors in angular velocity magnitude, angular acceleration magnitude, and linear acceleration magnitudes were about 11.9%, about 13.9%, and about 11.4% respectively, which are improved from the about 40%-80% NRMS errors observed in worst-case unconstrained mandible testing with the original mouthguard.

270 impacts were performed for this study; however nearly 41 (about 15%) of these impacts had an NRMS greater than the about 20% threshold between the reference and maxilla sensors to be excluded from the analysis. Because the majority of rejected impacts were in the PMHS, the human skull may not always act as a rigid body during certain impact conditions. While the ATD is made of a stiff polymer Delrin, the skull has a natural frequency near about 700 Hz. While this natural frequency is not in the range of the instrumented mouthguard, it is within the range of both the reference and maxilla sensors. Thus, impacts near either the maxilla or reference sensors that excite the natural frequency of the skull could introduce additional high frequency noise into the measurements.

While the validation result of other studies can be reproduced, it should be noted that free drop testing is used in this example instead of a linear impactor because drop tests are more convenient for PMHS heads. ATD heads were also tested using the free drop methodology so that effective comparison can be performed of results between the two systems to assess how well the ATD represented the more biofidelic PMHS. Experiment testing is confined to a maximum height of about 100 cm (maximum velocity of about 4.4 m/s). This represents the lower bound of impact severities tested in other validation studies; however, these speeds are still representative of the majority of football impacts. Finally, a single helmet and chinstrap model is used, while other models can alter jaw loads.

In conclusion, it is determined that the mandible constraint can affect the mouthguard accuracy in ATD and PMHS testing. The potential error mechanism is a second-order spring-mass system between the mouthguard EVA material and the ATD mandible near the sensors. Understanding the interaction between the mandible and mouthguard can direct device development that mitigates measurement errors. Mouthguard testing should include a freely articulating mandible to provide an upper bound on measurement error. In addition, the data shows that simplified ATD temporomandibular joints sufficiently reproduce more biofidelic PMHS mandible dynamics during drop testing for evaluating mouthguard measurement accuracy. The finding that mouthguard accuracy depends on mandible constraint may have implications on field data. It is also shown that mandible dynamics can be isolated from head kinematics measurement sensors using an improved mouthguard design. Employing such design, in combination with increasing sensor bandwidth to capture high frequency signals, should result in a highly accurate measurement device substantially independent of mandible dynamics.

Example 2

Evaluating Wearable Impact Sensors for Accuracy in Predicting Finite Element Measures Overview:

Wearable sensors designed to take measurements of head impacts have been validated for kinematics accuracy. However, with increasing use of finite element predicted tissue-based metrics as indicators for brain injury, it is desired to evaluate sensors for their ability to estimate tissue-based metrics as well. In this example, evaluation is performed of how errors in sensor kinematics can manifest as errors in tissue-based metrics. Comparison is performed of the performance of a mouthguard design that is susceptible to mandible disturbances against an improved design that mitigates these disturbances. Exploration is made of how rotating kinematic signals alters tissue-based measurements without affecting kinematic magnitude based accuracy measures. The results show that the improved design can predict both kinematics and tissue-based metrics well compared with the other design, demonstrating how kinematics errors from external disturbances can affect tissue-based metric estimates. In addition, the results show that rotating reference kinematics by about 30° results in over about 10% error in tissue-based metrics. This demonstrates that the transform used to rotate sensor signals to anatomically aligned axes should be accurate as well to predict tissue-based metrics. Through the analysis, it is demonstrated that evaluation of sensor kinematics errors is desired to better predict how sensors will perform at predicting tissue-based metrics.

Introduction:

Concussions are a leading cause of death and disability in the United States. The Center of Disease Control estimates about 3.5 million concussions occur annually in the United States alone; however, research has shown that this is likely an underestimate due to under-reporting. Concussions are often under-reported because concussion symptoms are subjectively evaluated and can be missed entirely or not associated with injury. Thus, an accurate, quantitative sensor and an associated sensitive threshold-based injury metric are desired for quantitative diagnosis.

Concussions are an injury to the brain usually resulting from trauma to the head. However, it is currently infeasible to observe the brain directly for injury in real-time. Thus, to investigate the cause of concussion and develop injury metrics, wearable sensor technologies are used to measure the severity of head trauma that results in concussion.

Wearable sensor technologies can be implemented in a variety of form factors. Three form factors are: sensors mounted on headgear; sensors mounted on skin; and sensors mounted on bony landmarks (instrumented mouthguard). The sensors are designed to measure the kinematics of the head during impact using a combination of linear accelerometers and angular gyroscopes. Using the sensors, kinematic head measurements can be collected, and kinematics-based injury metrics can be developed to predict the occurrence of concussions. However, these sensors and associated concussion metrics are still not in widespread use. This is because validation testing indicates that many sensors suffer from substantial errors in their kinematics accuracy, most commonly as a result of insufficient coupling to the skull (skin and headgear motion) or external disturbances (mandible interference).

Head kinematics are real-time measurable variables during a head impact. However, the brain is extremely deformable and has a complex geometry. As a result, approaches are developed to assess how the brain might react to measured kinematics using powerful finite element simulations of the brain during impact. These finite element simulations have allowed prediction of how the brain deforms, and is possibly damaged, by mechanical impacts to the head. This has prompted the development of tissue-based injury metrics, which unlike kinematics-based injury metrics, provide greater insight into how brain injury occurs.

One prevailing theory underlying brain injury is axons strain in the corpus callosum. Excess strain in the axons is thought to disrupt microtubule networks, while the corpus callosum represents an important relay of axons bridging the two brain hemispheres. This theory is supported by finite element simulations demonstrating that excess axon strain in the corpus callosum is predictor of brain injury. In addition, animal research and imaging studies have also shown changes in the corpus callosum region following concussion.

With the emergence of tissue-based metrics for predicting concussion, it is desired that wearable sensors should be able to estimate tissue-based measures accurately. While most sensors are evaluated on their ability to predict peak kinematics magnitude measurements, this is likely insufficient for estimating their ability to estimate tissue-based measurements. This is because the highly viscoelastic response of the brain is dependent on the time-history of head kinematics, and the geometrically complex shape of the brain is dependent on the direction of kinematic input.

In this example, evaluation is performed of how errors in sensor kinematic measurements and errors in transforming sensor kinematics from the sensor-fixed frame to a frame aligned with head anatomical axes manifest in measuring tissue-based metrics in American football. Tissue-based measurement accuracy is related with kinematic accuracy measures to demonstrate how kinematic accuracy measures are insufficient to describe tissue-based accuracy. Explanation is made of improved kinematics based metrics that are better able to predict resulting tissue-based accuracy while allowing omission of computationally taxing finite element simulations.

Methods:

To assess how errors in sensor kinematic measurements and errors in transforming sensor kinematics to the head center of mass manifest in measuring tissue-based metrics, use is made of impact data collected from laboratory experiments with an instrumented mouthguard in an anthropomorphic test dummy (ATD). To explore how sensor kinematic measurement errors manifest in tissue-based metrics, comparison is made of the performance of a comparative mouthguard and an improved version of the mouthguard designed to mitigate mandible disturbances. To explore how transformation errors manifest in tissue-based metrics, evaluation is performed of how tissue-based metrics change when ATD kinematic measurements are rotated.

Kinematic Measurement Errors Test Data

Figure 13:
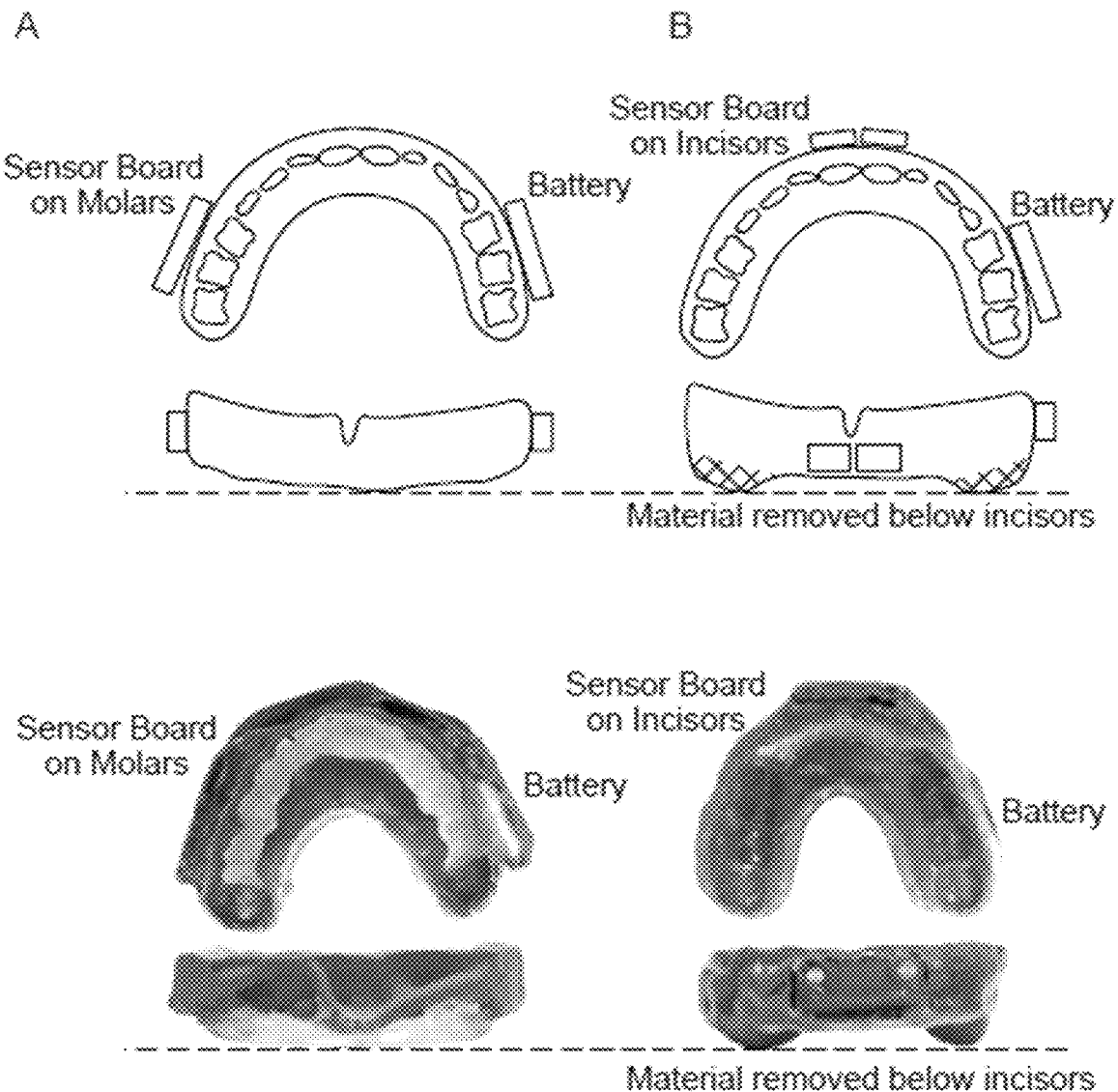
FIG. 13: Mouthguard Designs. (A) Comparative design of an instrumented mouthguard has poor kinematic accuracy due to disturbances from the mandible. (B) Improved design mitigates mandible disturbances by moving the sensors in front of the incisors and removing material in the bite plane.

Both instrumented mouthguard designs (FIG. 13) were custom formed to the ATD dentition. Both included a tri-axial linear accelerometer sampling at about 1000 Hz and a CFC180, fourth-order butterworth filter at about 300 Hz. Additionally, both included a tri-axial gyroscope. However, the comparative design used a sampling rate of about 1000 Hz and a fourth-order butterworth filter at about 184 Hz, while the improved design used a sampling rate of about 8000 Hz and a CFC180, fourth-order butterworth filter at about 300 Hz. The gyroscope bandwidth was increased in the improved design to more fully capture kinematics-based and tissue-based dynamics. Angular velocity signals were then differentiated with a fourth-order stencil to obtain angular acceleration.

Mouthguards were then equipped in a $50^{th}$ percentile X2 headform with an articulating mandible. The headform was equipped with a tri-axial linear accelerometer and a tri-axial gyroscope at the center of mass collecting data at about 100 kHz. Linear accelerometer signals were filtered at CFC1000 (fourth-order butterworth filter at about 1650 Hz), while angular gyroscope signals were filtered at CFC180 (fourth-order butterworth filter at about 300 Hz). As with the mouthguards, the angular velocity signals were differentiated using a fourth-order stencil to obtain angular acceleration. The mandible was left unconstrained and free to articulate to exercise the worst-case scenario for the instrumented mouthguards.

The mouthguard equipped ATD was fitted into a medium size Riddell Speed helmet and hoisted to a specified height and specified orientation. This allowed tests to exercise impact scenarios commonly seen in American football. Selected drop heights include: about 10 cm, about 60 cm, and about 100 cm, which resulted in impacts ranging from about 15 g-150 g, and selected impact locations include: vertex, frontal, frontal oblique right (oblique), parietal, occipital, and facemask impact locations. Three trials are performed for each combination of mouthguard, drop height, and impact location. This resulted in a total of 54 drop impacts for each mouthguard.

Transformation Errors Test Data

To explore how errors in transforming sensor kinematics might manifest in tissue-based metrics, rotation is performed on ATD reference kinematics obtained using the improved design. For each impact location, the final trial for the most severe impact severity (about 100 cm) is used. The signal is rotated about the anatomical x-axis (anterior-posterior), y-axis (left-right), and z-axis (superior-inferior) at about −30°, about −20°, about −10°, about 10°, about 20°, and about 30°. Measures from the rotated trials were compared against their baseline trials to assess errors.

Kinematics Analysis

To assess kinematic accuracy, use is made of a combination of metrics and improved analyses. Sensor accuracy can be assessed by comparing reference peak kinematic magnitude measures against sensor peak kinematic magnitude measures. Linear acceleration, angular velocity, and angular acceleration are kinematic measures that can be compared. A linear regression with fixed 0-intercept and an average relative difference are used to compare measures from the reference and the instrumented mouthguards or rotated ATD traces. In particular, a relative error is computed according to an absolute value of the difference between peak reference kinematic measure and peak-to-peak sensor kinematic measure normalized by the peak reference kinematic measure. In addition, evaluation is performed of sensor accuracy with an average relative difference of kinematics components, and the error in kinematics instantaneous axis (see below equation). These metrics were chosen to represent errors in kinematics directionality. The instantaneous axis error at a specified point in time is the angle between the reference kinematics vector (ref) and the sensor kinematics vector (mg).

$$\text{relatiave error} = \frac{\text{abs}(ref - mg)}{ref}$$

$$\text{Intantaneous Axis } Error_t = a\cos\left(\frac{\vec{ref}_t}{\|\vec{ref}_t\|} \cdot \frac{\vec{mg}_t}{\|\vec{mg}_t\|}\right)$$

Tissue-Based Metric Analysis

Figure 14:
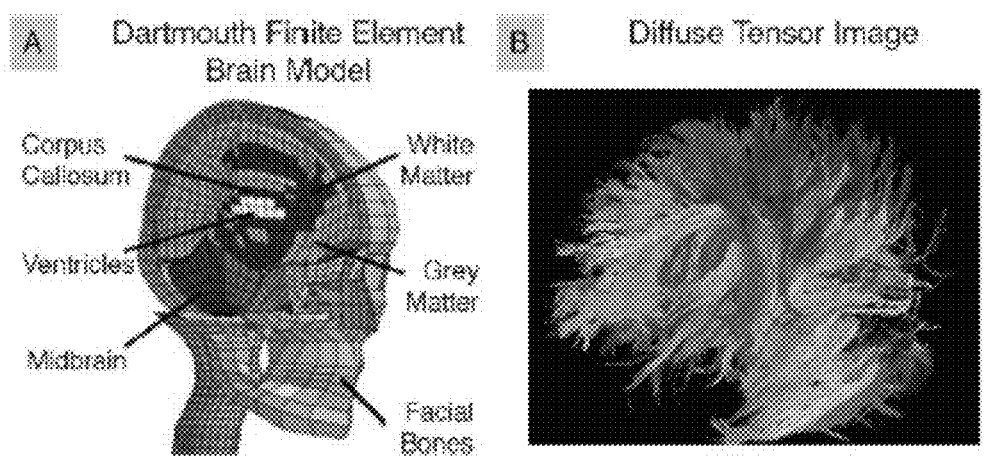
FIG. 14: Dartmouth Finite Element Model. (A) The Dartmouth finite element model has various elements and partitions the brain into several regions of interest, including the cortex, corpus callosum, and brain stem. (B) In addition, the Dartmouth finite element model can be used to predict axon-aligned strain and strain rates by projecting values onto DTI fiber tracts.

To calculate tissue-based metrics, the Dartmouth finite element model is used to simulate kinematics obtained from the ATD reference, instrumented mouthguards, and rotated ATD traces (FIG. 14). The Dartmouth finite element model is validated against tagged brain image data in cadaver impacts and can be used to assess tissue-based measures of injury-level impacts. The Dartmouth finite element model can also predict axon-aligned strains and strain rates by projecting tissue strain and strain rate tensors onto fiber tracts obtained from diffuse tensor imaging (DTI) (FIG. 14).

For the tissue-based analysis, calculation is performed of a combination of tissue-based metrics and improved analyses. Tissue-based metrics that can be used include Cumulative Strain Damage Measure (CSDM), population principal strain and strain rate measures (pop), and peak principal strain and strain rate measures. CSDM measures the number of elements that exceed a certain principal strain value over an entire simulation. For the analysis, 5%, 10%, and 20% thresholds are used. Population measures represent the principal strain or strain rate measure under which a certain percentage of elements fall. For the analysis, 95%, 90%, and 50% are used. Finally, peak principal strain and strain rate measures evaluate the peak measure over the region of interest in a simulation. To assess sensor accuracy, linear regressions are performed with fixed 0-intercept and an average relative difference is used to compare measures from the reference and the instrumented mouthguards or rotated ATD traces.

In addition to these metrics, additional measures are evaluated for assessing tissue-based sensor accuracy. First, the peak principal strain or strain rate over each element is obtained, and an element-wise comparison is made between the reference estimate and the instrumented mouthguard or rotated estimate. While there're some similarities to the peak principal strain and strain rate analysis, the peak principal strain and strain rate analysis typically does not take into account the location of peak measurement. Thus, an element-wise analysis gives a distribution of peak errors over regions of interest.

Second, calculation is performed of the axon-aligned strain and strain rate by projecting tissue strains and strain rates along DTI fiber tracts. Because axon-aligned strain has been identified as a potential mechanism for brain injury, it is desired to evaluate a sensor's ability to accurately measure this tissue-based metric.

Correlation Analysis

Finally, a correlation analysis is performed between kinematic measurement errors and tissue-based measurement errors to determine if any kinematic measurement errors predict tissue-based measurement errors well. Because finite element simulations are computationally expensive, being able to estimate tissue-based accuracy using kinematic accuracy measures is desirable for validation.

Results:

Instrumented Mouthguard Accuracy

Figure 15:
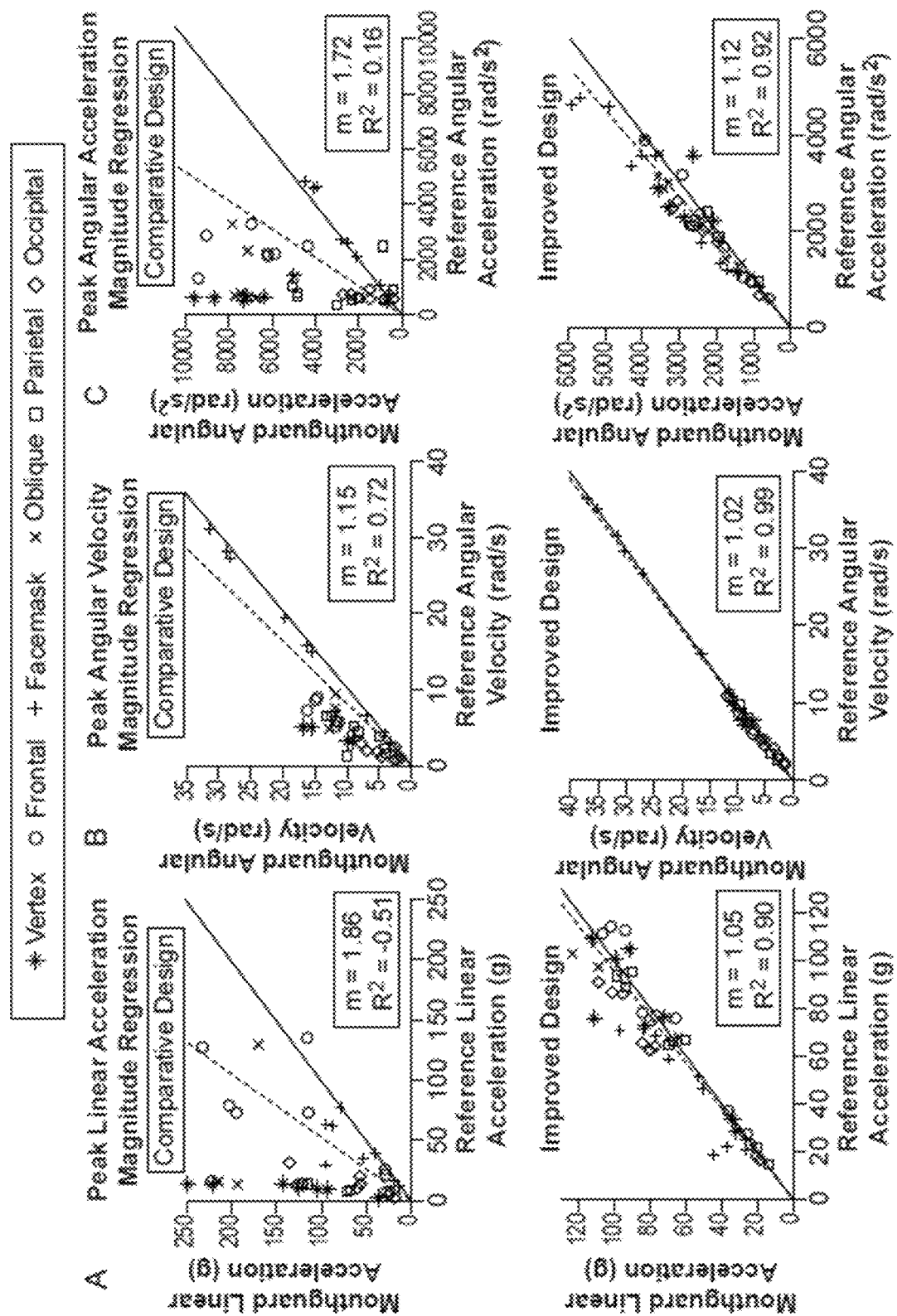
FIG. 15: Kinematics Regressions. Linear regressions with fixed 0-intercept comparing (A) peak linear acceleration magnitude, (B) peak angular velocity magnitude, and (C) peak angular acceleration magnitude between the reference and the comparative design or improved design.
Figure 16:
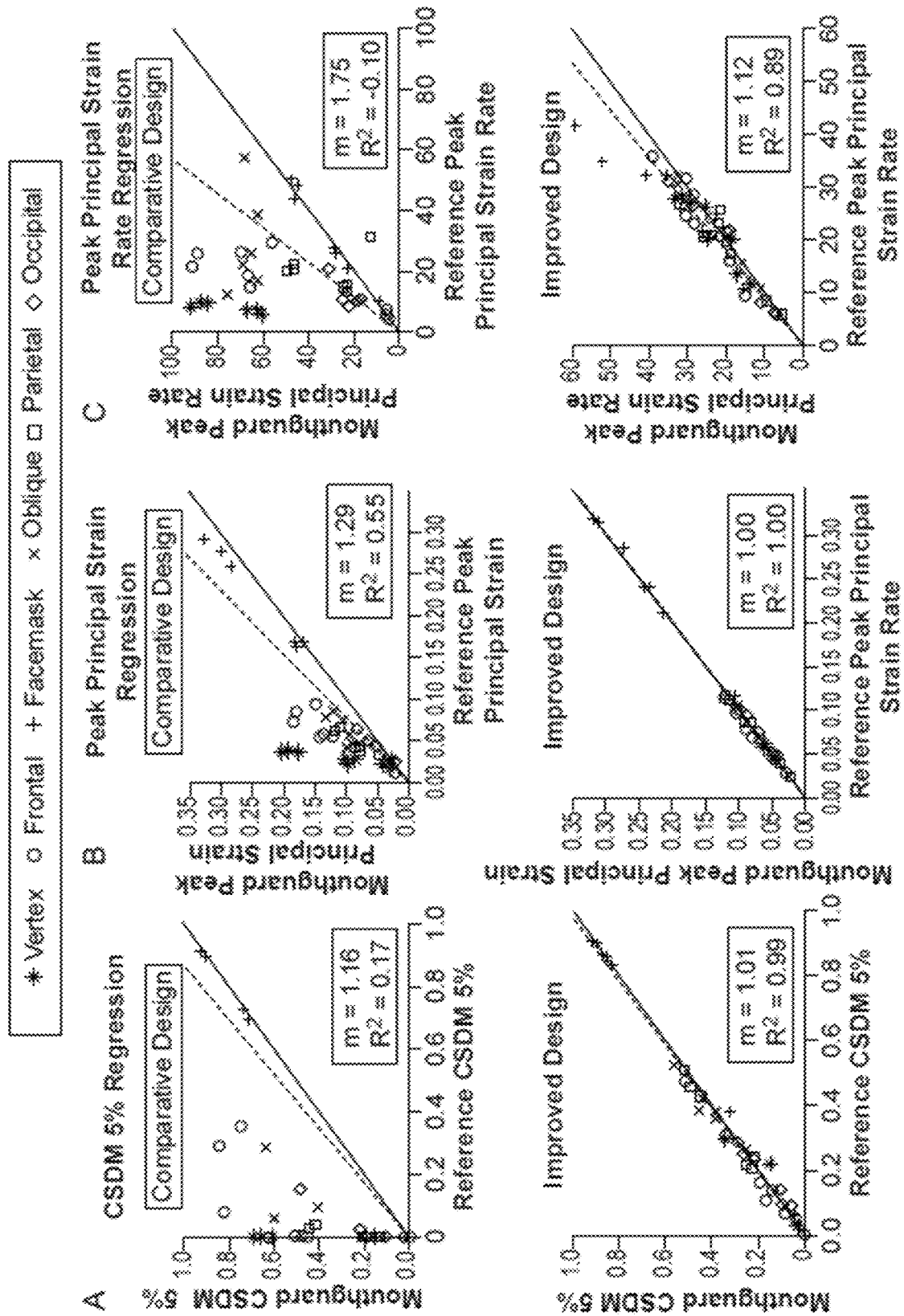
FIG. 16: Tissue Regressions. Linear regressions with fixed 0-intercept comparing (A) CSDM 5%, (B) peak principal strain, and (C) peak principal strain rate between the reference and the previous design or improved design.

First, results are presented for both the comparative mouthguard and improved mouthguard against their respective ATD references. Linear regressions are presented with forced 0-intercept for peak linear acceleration magnitude, peak angular velocity magnitude, and peak angular acceleration magnitude as representative kinematics accuracy (FIG. 15). Also presented is linear regression with forced 0-intercept for CSDM 5%, peak principal strain, and peak principal strain rate (FIG. 16).

The comparative design significantly overestimates angular acceleration and slightly overestimates angular velocity. The comparative design also overestimates linear acceleration. Instead of comparing kinematics at the mouthguard location, comparison is performed of kinematics at the head center of mass. Regressions for the improved design show significantly better accuracy.

Trends for the tissue-based regression show similar trends. The comparative design performs significantly worse than the improved design at estimating tissue-based metrics. In addition, the regressions for strain in for both mouthguards are qualitatively similar to the respective angular velocity regression. The same is true for regressions of strain rate and angular acceleration.

Figure 17:
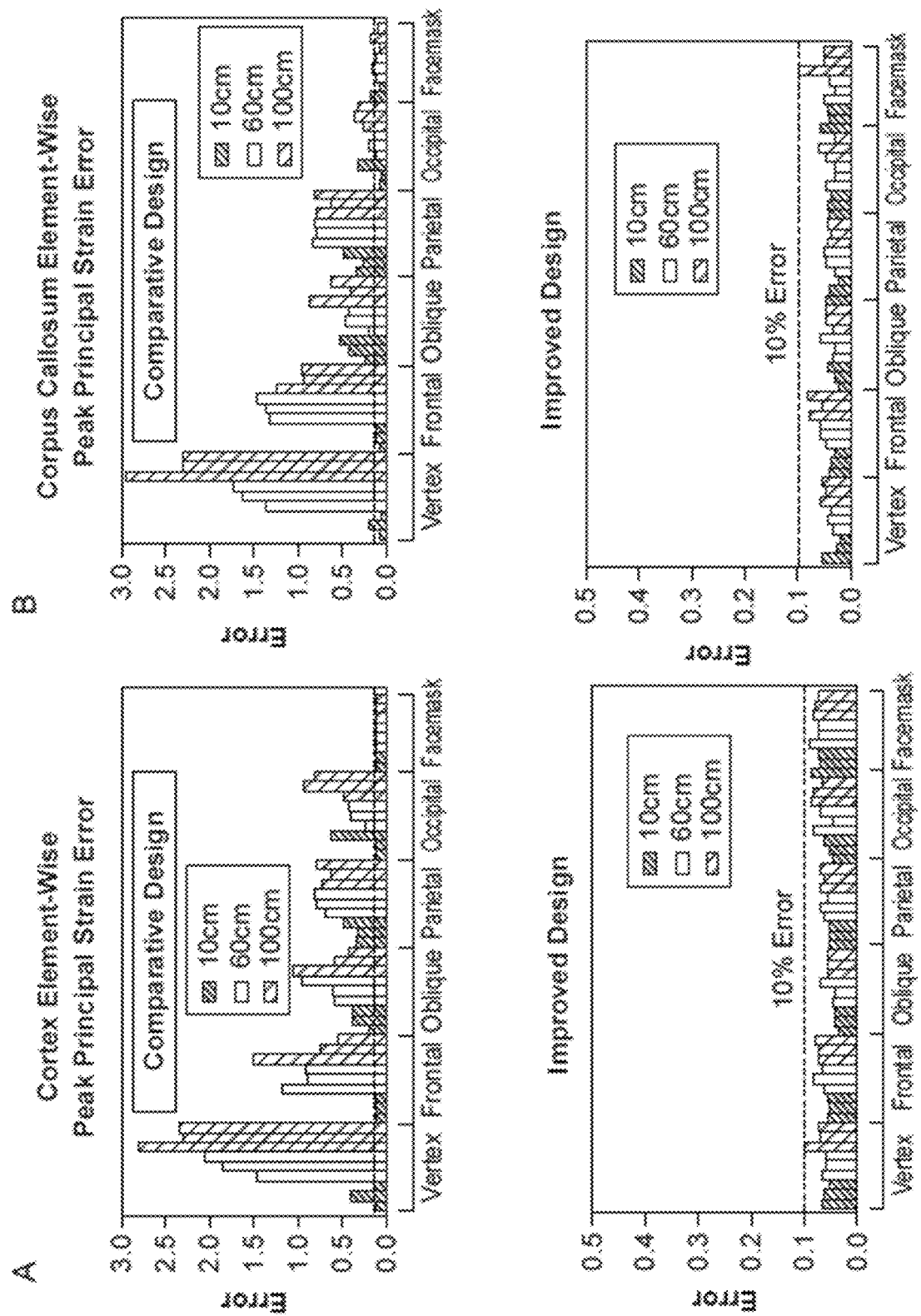
FIG. 17: Element-wise Peak Principal Strain Errors. Computation is performed of the average element-wise peak principal strain error in (A) the cortex, (B) the corpus callosum, and (C) the brain stem for both the comparative design and improved design. The improved design has far superior accuracy when compared with the comparative design.
Figures 17, 18:
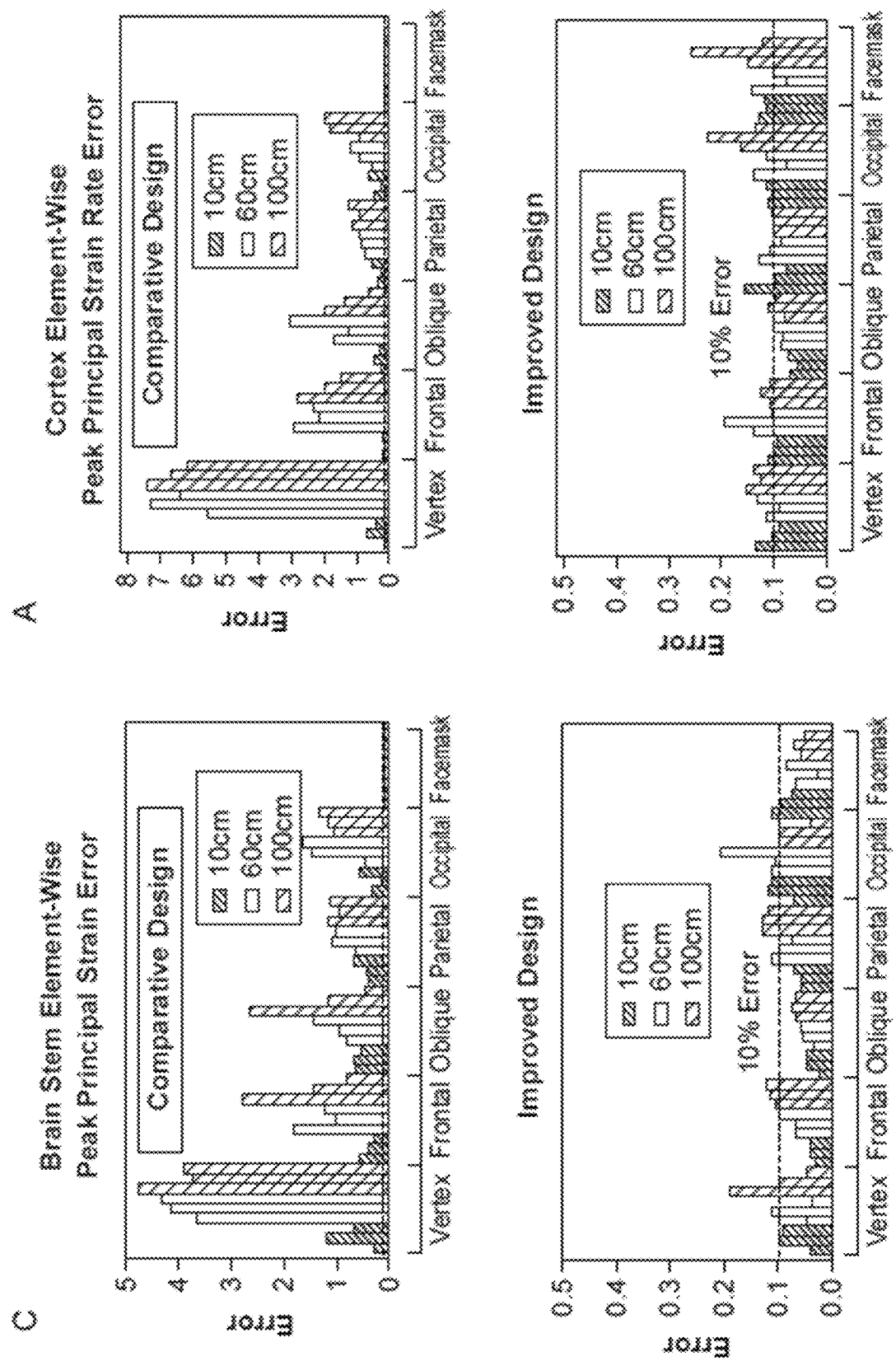
FIG. 18: Element-wise Peak Principal Strain Rate Errors. Computation is performed of the average element-wise peak principal strain rate error in (A) the cortex, (B) the corpus callosum, and (C) the brain stem for both the comparative design and improved design. Again the improved design has far superior accuracy when compared with the comparative design.
Figure 18:
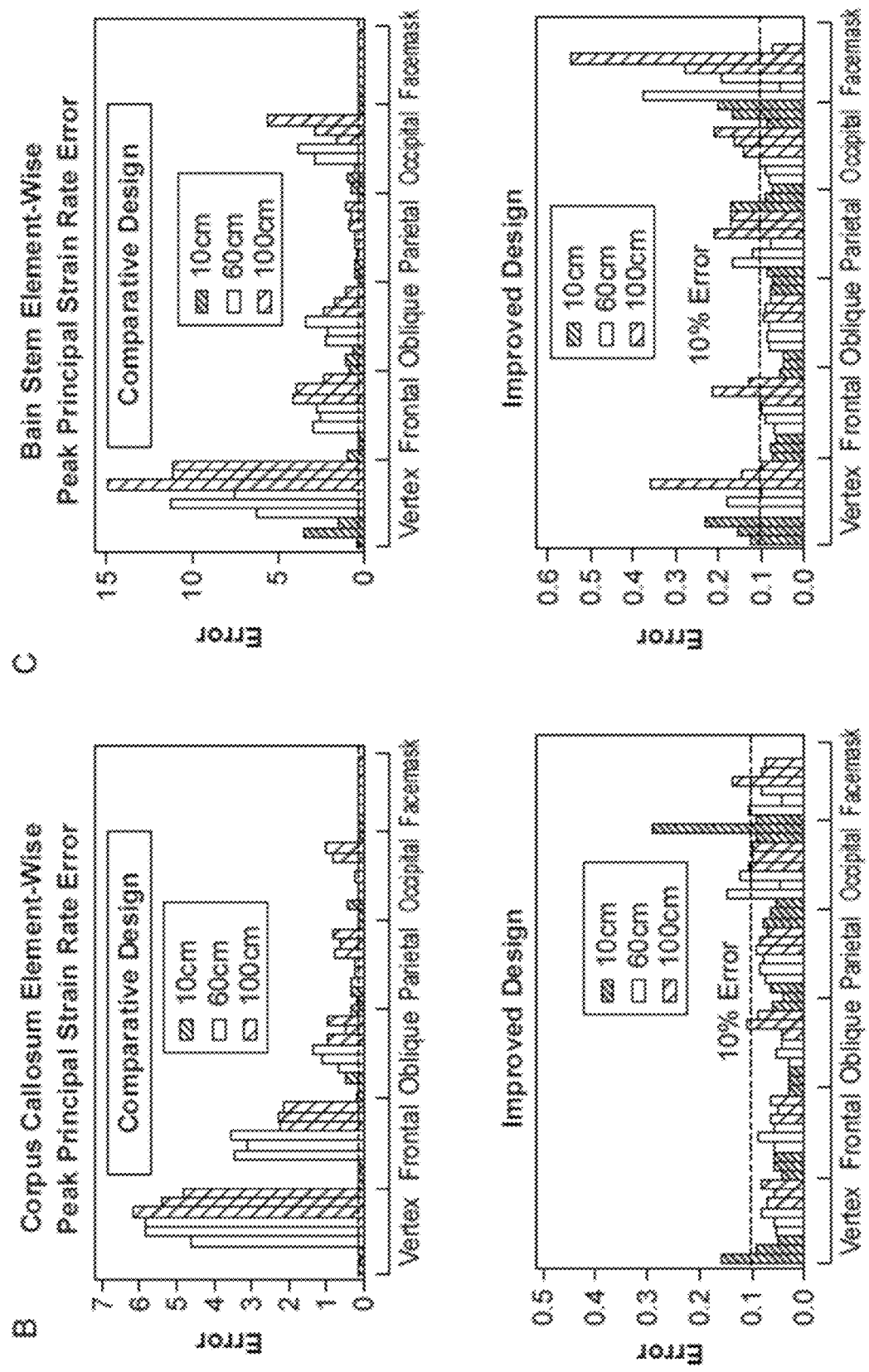

Next, analysis is performed of the average element-wise peak principal strain (FIG. 17) and strain rate (FIG. 18) errors in the cortex, the corpus callosum, and the brain stem. Again, the comparative design has significant errors in element-wise predictions of peak principal strain and peak principal strain rate, whereas the improved design predicts element-wise peaks within about 10% for the majority of trials. In particular, the comparative design performed the worst in predicting element-wise peak metrics in vertex impacts. Both mouthguards had worse accuracy at predicting element-wise peak principal strain rate than element-wise peak principal strain. Finally, estimates of element-wise peak metrics were overall worst in the brain stem and overall best in the corpus callosum.

Figure 19:
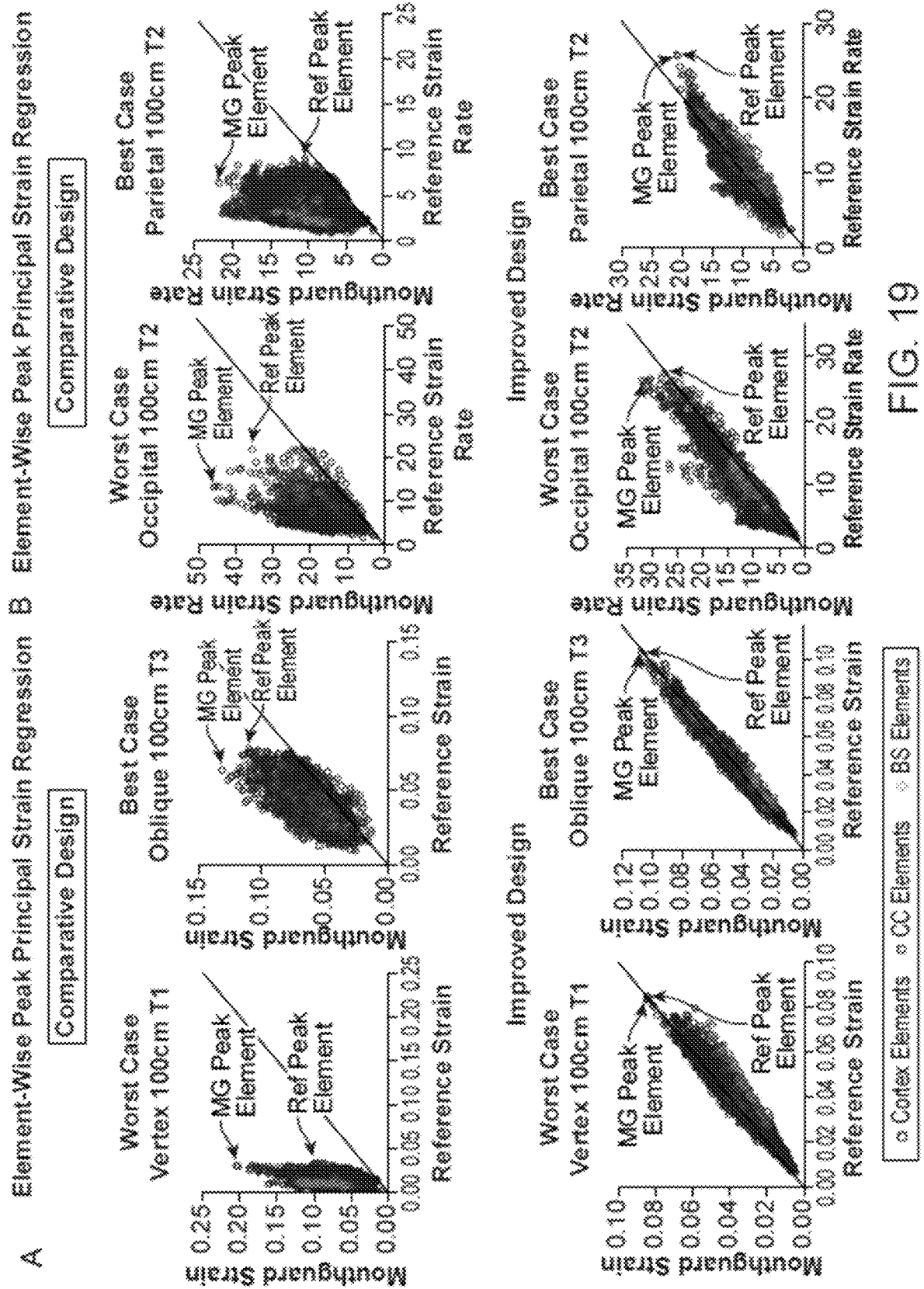
FIG. 19: Element-wise comparison: (A) Comparison is performed of representative best and worst cases from each mouthguard design to demonstrate element-wise peak principal strain errors. In the comparative design, errors result from both global overestimation and from large estimation variance. In addition, in most cases from the comparative design, the element with the peak principal strain in the reference is not the same as the element with the peak principal strain in the comparative design. The same trend is observed in (B) representative of best and worst cases from each mouthguard design for principal strain rate errors.
Figure 20A:
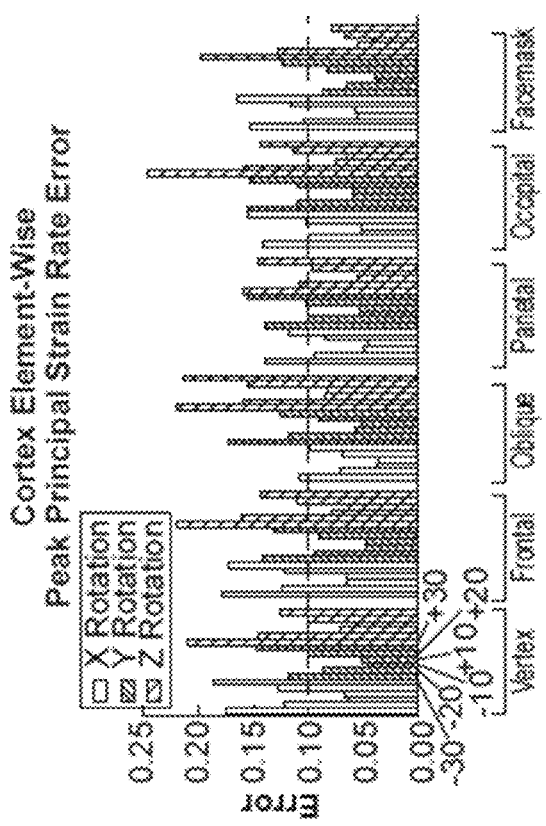
FIG. 20: Element-wise Peak Principal Errors after Rotation. Computation is performed of the average element-wise peak principal strain and strain rate error in (A, B) the cortex, (C, D) the corpus callosum, and (E, F) the brain stem between rotated ATD references and their baseline. An about 30° rotation results in the greatest errors in all cases. Rotations about the z-axis produce the largest errors compared to rotations about the x-axis and y-axis, and element-wise measures in the corpus callosum are the most sensitive to rotations.
Figure 20B:
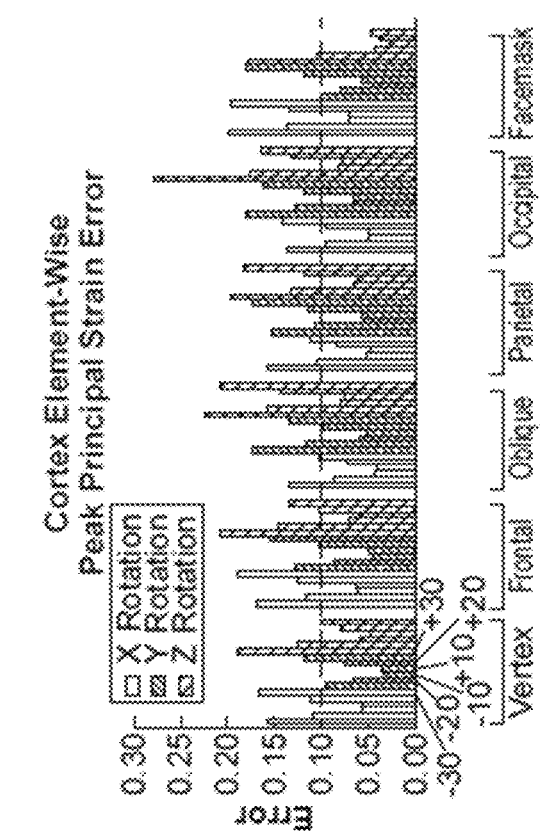
Figure 20C:
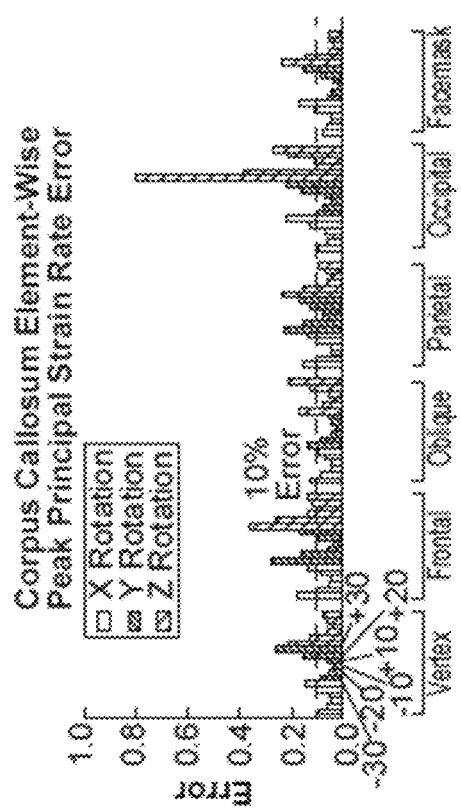
Figure 20D:
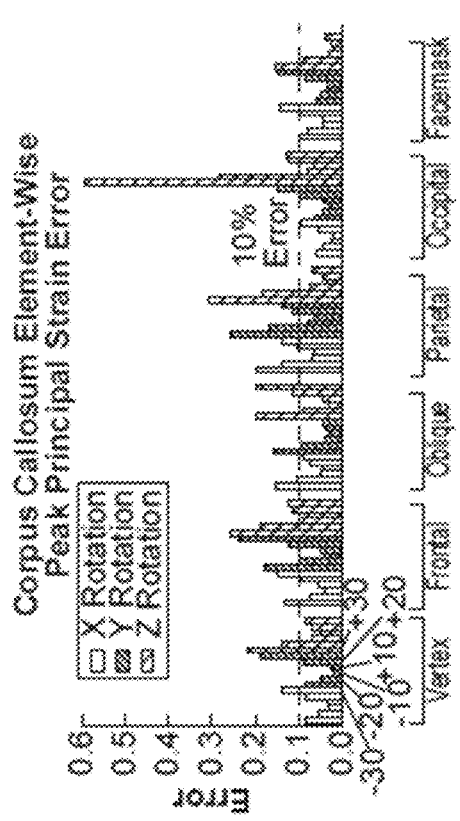
Figure 20F:
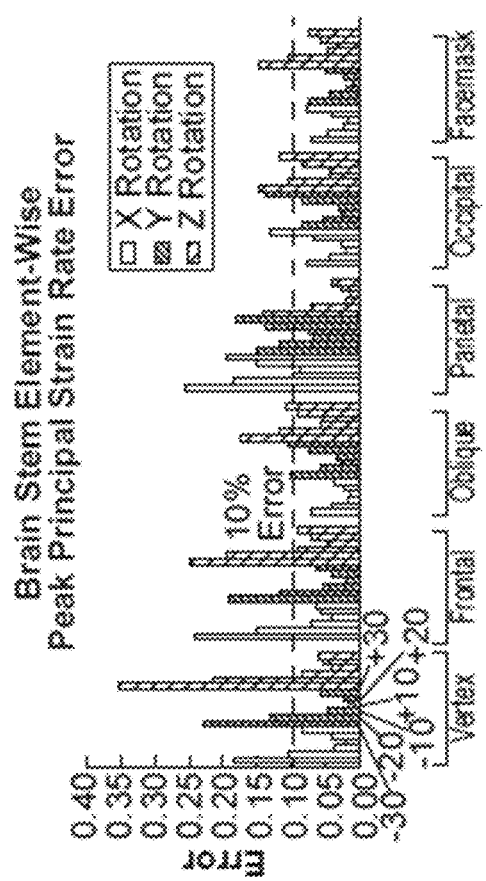
Figure 20E:
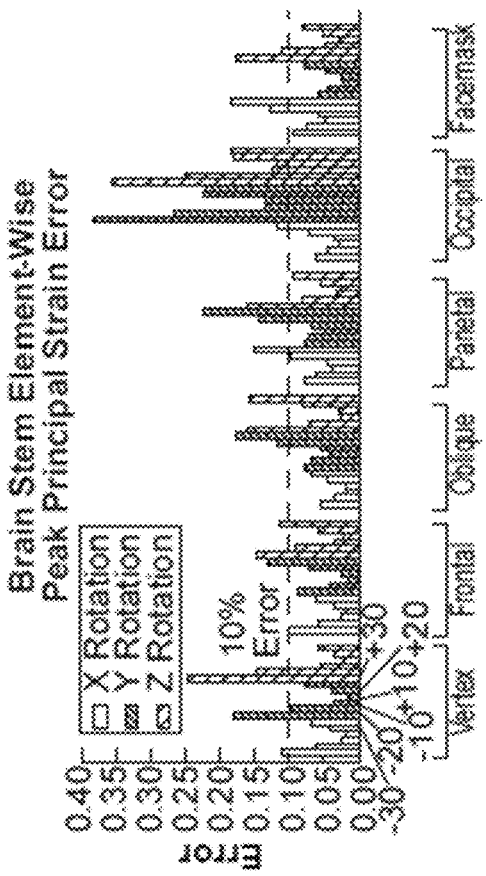

The element-wise peak principal strain and strain rate results demonstrate that there may be a distribution of errors over the elements of each brain region. This is not captured when comparing global peak principal strain and strain rate. To emphasize this, the peak principal strain and strain rate in each element are plotted for the cortex, corpus callosum, and brain stem for representative cases (FIG. 19). From this analysis, it can be seen that the element with peak principal strain or strain rate for the mouthguard does not necessarily correspond to the element with peak metric in the ATD reference. In addition, element-wise errors are seen for the comparative design result from a combination of global overestimation (worst case, vertex 100 cm T1 element-wise peak principal strain) and large variance (best case, oblique 100 cm T3 peak principal strain).

Errors from Sensor Transformation

Next, analysis is performed of results from the rotated ATD reference trials. Because rotations conserve kinematic magnitudes, there are no errors in kinematic magnitude measures. Thus, average element-wise peak principal strain and strain rate between rotated ATD trials and their baseline are presented (FIG. 20). Increasing rotation produced greater errors. Strikingly having an error in rotation of about 30° generally results in average element-wise errors above about 10%. In addition, rotations about the z-axis have the greatest errors. Finally, average element-wise errors in the corpus callosum are the most sensitive to rotation of baseline kinematics.

Correlation Analysis

Finally, a correlation analysis is performed between kinematic errors and finite element tissue-based measurement errors. This correlation is performed over all data collected, comparing the two mouthguard designs and rotated reference against their respective ATD reference and baseline traces. For the kinematic errors, the following kinematic metrics are used: peak and NRMS linear acceleration magnitude error; peak and NRMS angular velocity magnitude error; and peak and NRMS angular acceleration magnitude error. Also included are peak kinematic x-, y-, and z-components and peak instantaneous axis errors.

For tissue-based measurement errors, the following metrics are used: global peak principal strain error; global peak principal strain rate error; CSDM 5%, 10%, and 20% error; pop 95%, 90%, and 50% principal strain error, and pop 95%, 90%, and 50% principal strain rate error. Also included are average element-wise peak principal strain and strain rate errors.

Figure 21:
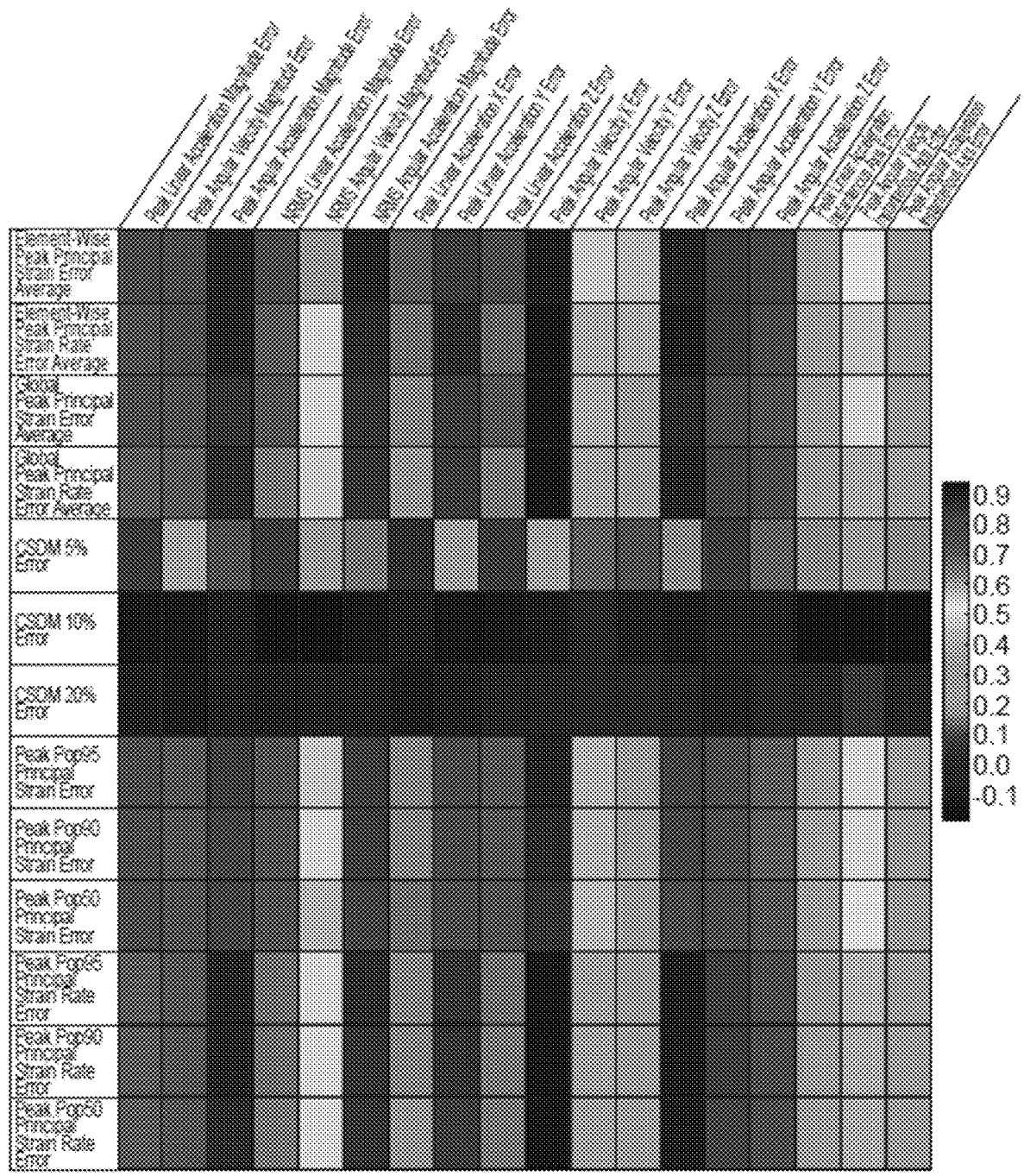
FIG. 21: Correlation of Kinematic Errors with Tissue-based Metric Errors. CSDM 5%, 10%, and 20% have poor correlation with kinematics error metrics. Errors in peak angular velocity and angular acceleration x-axis correlate best with all other tissue-based measures. In addition, peak kinematic magnitude errors correlate well with tissue-based metric errors.

The correlation analysis (FIG. 21) shows that error in peak angular velocity about the x-axis and error in peak angular acceleration about the x-axis correlates best with most tissue-based error metrics. Peak kinematics magnitude errors also correlate well with most tissue-based metric errors, and, interestingly, NRMS kinematics magnitude errors have worse correlation. Finally, CSDM 5%, 10%, and 20% errors have poor correlation with all evaluated kinematic-based errors.

Discussion:

In this example, an analysis is presented of how sensor kinematic errors can manifest in tissue-based metric errors. Specifically, evaluation is performed on two sources of sensor kinematic errors. The first source of error is caused by external disturbances, which is explored using a comparative mouthguard that has significant error as a result of mandible disturbances, and an improved mouthguard that is designed to mitigate these disturbances. The second source of error is caused by discrepancies in transforming sensor kinematics from the sensor frame to a frame aligned with head anatomical axes, which is represented by rotating ATD reference kinematics.

Both sources of kinematics error produce errors in tissue-based estimates following simulation with the Dartmouth finite element simulation. The comparative mouthguard experiences poor accuracy in both kinematic measurements and tissue-based metrics, while the improved mouthguard has excellent accuracy in both cases. This shows that disturbances resulting in kinematic errors can also propagate into tissue-based metric errors. This has implications for data collected by systems that have kinematic errors, as these errors likely propagate to tissue-based metrics.

More importantly, the effect of rotating kinematic signals on tissue-based metrics is demonstrated. The results show that an about 30° rotation of the kinematics generally results in over about 10% tissue-based metric errors. This implies that even with a perfect measurement sensor, it is still possible to have errors in tissue-based metrics. This is because wearable sensors cannot be placed at the head center of mass and sensor kinematics should be rotated to head anatomical coordinates and transformed to the center of mass. Thus, a perfect sensor with an imperfect estimate of this transform can have errors in tissue-based metrics.

Figure 22:
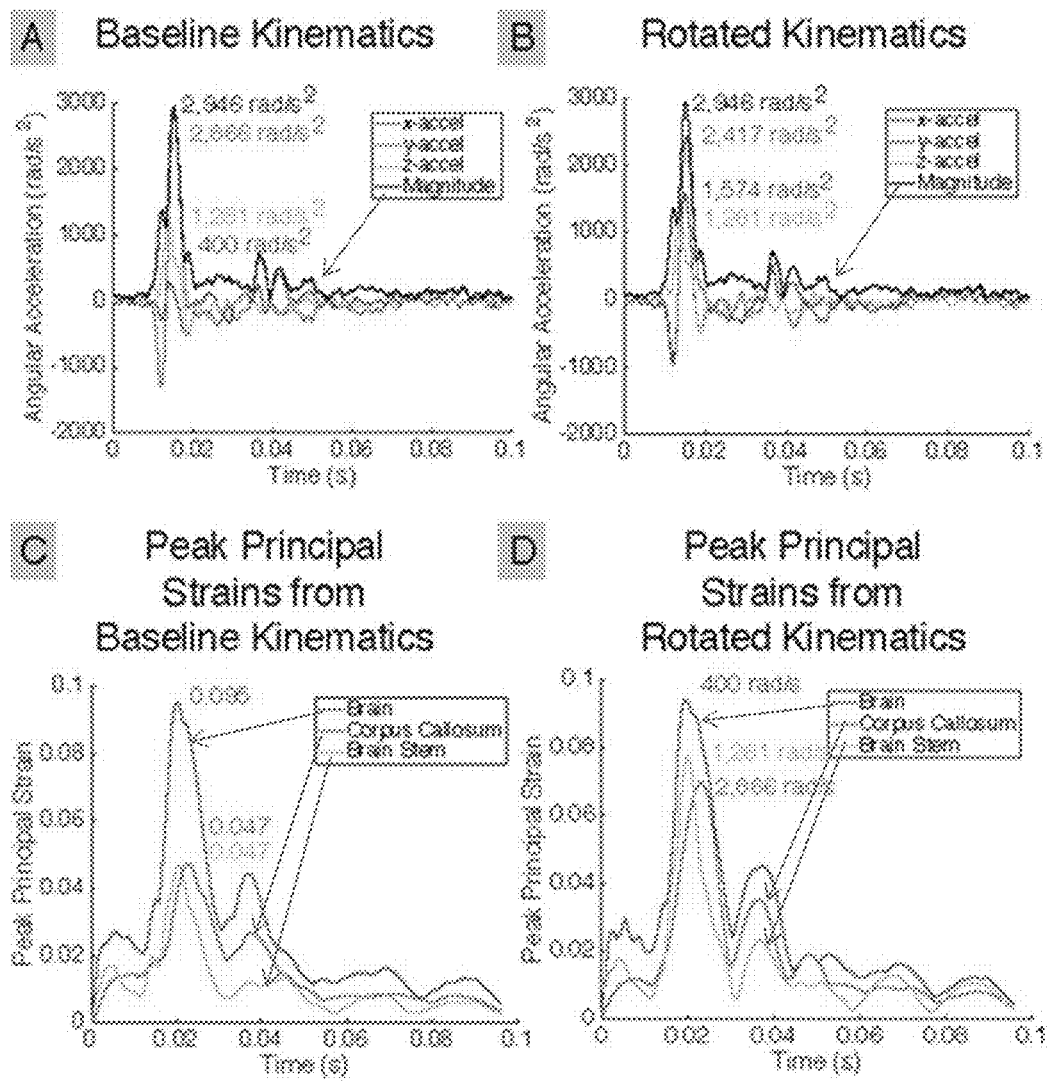
FIG. 22: Rotating Kinematics. (A) Baseline angular acceleration kinematics. Magnitude angular acceleration does not change after (B) rotation; however, components are affected. Because finite element simulations are directionally dependent, (C) tissue-based metrics change following rotation (D).

Finally, the correlation analysis demonstrates that errors in kinematic magnitude measurements may be sufficient to predict performance for estimating tissue-based metrics. However, directional errors, particularly errors in x-axis angular velocity and x-axis angular acceleration, may be better at predicting accuracy in measuring tissue-based metrics. This is made especially clear in the rotated ATD reference data set. FIG. 22 demonstrates that rotating kinematics does not affect kinematic magnitude, and thus kinematic magnitude accuracy measures will show that the sensor has perfect accuracy. However, the kinematic components are affected by rotation, and because finite element results are directionally dependent, tissue-based metrics can also be affected.

Thus, while assessing kinematic magnitude error may indicate how a sensor might perform at estimating tissue-based metrics, it is also important to also assess how sensors estimate kinematic components because of the directional dependence of the brain and finite element simulations.

This example has demonstrated how sensor kinematic measurement errors may manifest in tissue-based metric errors. The results also demonstrate the importance of carefully evaluating sensor kinematic accuracy to understand how it might affect estimates of tissue-based metrics, and the importance of obtaining an accurate transform from the sensor to the head center of mass to obtain accurate kinematic component measures. This example has also demonstrated the capability of the improved mouthguard design for measurement of both kinematics and tissue-based metrics.

Spatial descriptions, such as "above," "below," "up," "left," "right," "down," "top," "bottom," "vertical," "horizontal," "side," "higher," "lower," "upper," "over," "under," and so forth, are indicated with respect to the orientation shown in the figures unless otherwise specified. It should be understood that the spatial descriptions used herein are for purposes of illustration only, and that practical implementations of the embodiments described herein can be spatially arranged in any orientation or manner, provided that the merits of embodiments of this disclosure are not deviated by such arrangement.

As used herein, the singular terms "a," "an," and "the" may include plural referents unless the context clearly dictates otherwise. Thus, for example, reference to an object may include multiple objects unless the context clearly dictates otherwise.

As used herein, the terms "substantially," "substantial," and "about" are used to describe and account for small variations. When used in conjunction with an event or circumstance, the terms can refer to instances in which the event or circumstance occurs precisely as well as instances in which the event or circumstance occurs to a close approximation. When used in conjunction with a numerical value, the terms can refer to a range of variation of less than or equal to ±10% of that numerical value, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%.

Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

While the disclosure has been described with reference to the specific embodiments thereof, it should be understood by those skilled in the art that various changes may be made and equivalents may be substituted without departing from the true spirit and scope of the disclosure as defined by the appended claims. In addition, many modifications may be made to adapt a particular situation, material, composition of matter, method, operation or operations, to the objective, spirit and scope of the disclosure. All such modifications are intended to be within the scope of the claims appended hereto. In particular, while certain methods may have been described with reference to particular operations performed in a particular order, it will be understood that these operations may be combined, sub-divided, or re-ordered to form an equivalent method without departing from the teachings of the disclosure. Accordingly, unless specifically indicated herein, the order and grouping of the operations is not a limitation of the disclosure.

What is claimed is:

1. An oral appliance, comprising:
   a body defining a channel to accommodate an upper dentition, wherein the body is formed of ethylene vinyl acetate (EVA) material; and
   a motion sensor,
   wherein the body includes a front portion that is formed to accommodate an incisor area of the upper dentition, and the motion sensor is affixed to the front portion adjacent to the incisor area, and
   wherein the body further includes a pair of rear portions connected by the front portion, and the rear portions are formed to accommodate respective molar areas of the upper dentition, and
   wherein the motion sensor has a data sampling rate of 2 kHz or greater, and
   wherein the front portion includes a gap formed in material of the body adjacent to the incisor area and the motion sensor so as to isolate the motion sensor affixed to the front portion from perturbations in the pair of rear portions.

2. The oral appliance of claim 1, wherein the rear portions include respective standoff regions.

3. The oral appliance of claim 1, wherein the motion sensor includes at least one of an accelerometer or a gyroscope.

4. The oral appliance of claim 1, wherein the data sampling rate is 5 kHz or greater.

5. The oral appliance of claim 1, wherein the perturbances are associated with bites occurring in connection with molar areas of the upper dentition.

6. An oral appliance, comprising:
   a body defining a channel to accommodate an upper dentition, wherein the body is formed of biocompatible material; and
   a motion sensor affixed to the front portion,
   wherein the body includes a standoff region sized to extend into a bite plane, and a first property of the biocompatible material in the standoff region is different from a second property of the biocompatible material of a remaining portion of the body that is separate from the standoff region, the remaining portion of the body defining the channel, and wherein the standoff region is formed to reduce oscillatory noise at the motion sensor originating from the bite plane,
   wherein the body includes a front portion and a pair of rear portions connected through the front portion, and
   wherein the front portion includes a gap formed in the material adjacent to an incisor area of the upper dentition between the front portion and the pair of rear portions, and wherein the gap is formed adjacent to the motion sensor.

7. The oral appliance of claim 6, wherein the rear portions include respective standoff regions.

8. The oral appliance of claim 6, wherein the motion sensor includes at least one of an accelerometer or a gyroscope.

9. The oral appliance of claim 6, wherein the first property comprises an elastomer and the second property comprises an ethylene vinyl acetate (EVA) material.

10. The oral appliance of claim 6, wherein the first property of the biocompatible material is a greater extension of the biocompatible material into the bite plane than the second property.

* * * * *